United States Patent
Kerns et al.

(10) Patent No.: US 10,076,359 B2
(45) Date of Patent: *Sep. 18, 2018

(54) ADJUSTABLE CANNULA SYSTEMS AND DEVICES

(71) Applicant: DOHENY EYE INSTITUTE, Los Angeles, CA (US)

(72) Inventors: Ralph Kerns, Laguna Niguel, CA (US); Prashant Bhadri, Pico Rivera, CA (US); Matthew McCormick, Forest Falls, CA (US); Anderson Gustavo Teixeira Pinto, Sao Paulo (BR); Mark Humayun, Glendale, CA (US); Luis Arana, Curitiba (BR)

(73) Assignee: DOHENY EYE INSTITUTE, Los Angeles, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 14/941,412

(22) Filed: Nov. 13, 2015

(65) Prior Publication Data

US 2016/0066951 A1    Mar. 10, 2016

Related U.S. Application Data

(63) Continuation of application No. 13/394,497, filed as application No. PCT/US2010/049722 on Sep. 21, 2010, now Pat. No. 9,198,797.

(Continued)

(51) Int. Cl.
   *A61B 17/34*    (2006.01)
   *A61F 9/007*    (2006.01)
   *A61B 17/00*    (2006.01)

(52) U.S. Cl.
   CPC ...... *A61B 17/3439* (2013.01); *A61B 17/3431* (2013.01); *A61F 9/007* (2013.01);
   (Continued)

(58) Field of Classification Search
   CPC ... A61B 17/3439; A61F 9/007; A61F 9/00736
   See application file for complete search history.

(56) References Cited

U.S. PATENT DOCUMENTS

| 3,509,883 A | 5/1970 | Dibelius |
| 3,788,318 A | 1/1974 | Kim et al. |

(Continued)

FOREIGN PATENT DOCUMENTS

| EP | 1 943 989 A1 | 7/2008 |
| WO | 2001/052753 | 7/2001 |
| WO | 2010/064062 | 6/2010 |

OTHER PUBLICATIONS

"Designer Materials" Army Logistician, PB 700-06-06 vol. 38, Issue 6. Nov.-Dec. 2006. http://www.alu.army.mil/alog/issues/NovDec06/designer_materials.html, printed on Jun. 11, 2015.

(Continued)

*Primary Examiner* — Ellen C Hammond
(74) *Attorney, Agent, or Firm* — Baker Botts L.L.P.

(57) ABSTRACT

Various adjustable cannula systems are provided. The systems can include an adjustable cannula capable of expansion and/or contraction having an elongate body with a distal end and a proximal end. The adjustable cannula can be coupled to an upper housing and a lower housing such that rotation of the upper housing results in expansion or contraction of the adjustable cannula. The adjustable cannula can also have a proximal end having a lumen larger than a distal end lumen. A plurality of flanges can be formed in the elongate body by a plurality of slits that span a majority of a length of the cannula, including along or proximate to its proximal end and distal end.

4 Claims, 18 Drawing Sheets

Related U.S. Application Data

(60) Provisional application No. 61/244,841, filed on Sep. 22, 2009.

(52) U.S. Cl.
CPC ............ *A61F 9/00736* (2013.01); *A61B 2017/00398* (2013.01); *A61B 2017/00867* (2013.01)

(56) References Cited

U.S. PATENT DOCUMENTS

| | | | |
|---|---|---|---|
| 3,815,608 A | 6/1974 | Spinosa et al. | |
| 4,411,655 A | 10/1983 | Schreck | |
| 4,608,965 A | 9/1986 | Anspach et al. | |
| 4,899,729 A | 2/1990 | Gill et al. | |
| 5,053,009 A | 10/1991 | Herzberg | |
| 5,139,511 A | 8/1992 | Gill et al. | |
| 5,273,529 A | 12/1993 | Idowu | |
| 5,273,530 A | 12/1993 | Del Cerro et al. | |
| 5,312,417 A | 5/1994 | Wilk | |
| 5,334,164 A | 8/1994 | Guy et al. | |
| 5,400,770 A | 3/1995 | Nakao et al. | |
| 5,431,676 A | 7/1995 | Dubrul et al. | |
| 5,460,170 A * | 10/1995 | Hammerslag | A61B 17/0293 600/201 |
| 5,674,240 A | 10/1997 | Bonutti et al. | |
| 5,795,289 A | 8/1998 | Wyttenbach | |
| 5,800,394 A | 9/1998 | Yoon et al. | |
| 5,944,691 A | 8/1999 | Querns et al. | |
| 5,957,832 A | 9/1999 | Taylor et al. | |
| 5,957,902 A | 9/1999 | Teves | |
| 6,033,426 A | 3/2000 | Kaji | |
| 6,183,493 B1 | 2/2001 | Zammit | |
| 6,238,370 B1 | 5/2001 | Neuhann et al. | |
| 6,371,968 B1 | 4/2002 | Kogasaka et al. | |
| 6,398,803 B1 | 6/2002 | Layne et al. | |
| 6,454,783 B1 | 9/2002 | Piskun | |
| 7,100,612 B2 | 9/2006 | Dunlap | |
| 7,163,510 B2 | 1/2007 | Kahle et al. | |
| 7,297,106 B2 | 11/2007 | Yamada et al. | |
| 7,449,011 B2 | 11/2008 | Wenchell et al. | |
| 7,967,776 B2 | 6/2011 | von Segesser | |
| 8,105,236 B2 | 1/2012 | Malandain et al. | |
| 2003/0199737 A1 | 10/2003 | Deslauriers et al. | |
| 2004/0087968 A1 | 5/2004 | Core | |
| 2004/0260327 A1 | 12/2004 | Mueller, Jr. et al. | |
| 2005/0059934 A1 | 3/2005 | Wenchell et al. | |
| 2005/0222576 A1 | 10/2005 | Kick et al. | |
| 2007/0106319 A1 | 5/2007 | Au et al. | |
| 2007/0149997 A1 * | 6/2007 | Muller | A61F 2/013 606/200 |
| 2007/0225568 A1 | 9/2007 | Colleran | |
| 2009/0131881 A1 | 5/2009 | Frisella, Jr. | |
| 2009/0177288 A1 | 7/2009 | Wallsten | |
| 2009/0270817 A1 | 10/2009 | Moreno et al. | |
| 2011/0054260 A1 | 3/2011 | Albrecht et al. | |
| 2011/0118552 A1 | 5/2011 | Fischvogt | |
| 2013/0204092 A1 | 8/2013 | Hannaford et al. | |
| 2014/0046299 A1 | 2/2014 | Shelton, IV | |

OTHER PUBLICATIONS

Assi et al., Reversed Self-Sealing Pars Plana Sclerotomies, 2000, vol. 20, Issue 6, pp. 689-692.
Bhende et al., Ophthalmology, Sep. 2000, vol. 107, Issue 9.
Boker et al., Ultrasound Biomicroscopy for Examination of the Scelerotomy Site After Pars Plana Vitrectomy, Dec. 1994, vol. 118, Issue 6.
Claus Eckardt, Retina, The Journal of Retinal and Vitreous Diseases, 2005.
Fujii et al., Ophthalmology, Oct. 2002, vol. 109, Issue 10.
Hatta et al., Ultrasound Biomicroscopy for Examination of the Scelerotomy Site in Eyes with Proliferative Diabetic Retinopathy After Vitrectomy, 2000, vol. 20, Issue 1, pp. 52-58.
Howard F. Fine, Ophthalmology, Jun. 2007, vol. 114, Issue 6.
Jackson, American Journal of Ophthalmology, Jan. 2000, vol. 129, Issue 1, pp. 116-117.
Kwok et al., American Journal of Ophthalmology, Jun. 1999, vol. 127, Issue 6, pp. 731-733.
Kwok et al., Ultrasound Biomicroscopy of Conventional and Sutureless Pars Plana Sclerotomies: A Comparative and Longitudinal Study, Aug. 2001, vol. 132, Issue 2, pp. 172-177.
Rahman, Self-Sealing Sclerotomies for Sutureless Pars Plana Vitrectomy, Nov. 2000, vol. 31, Issue 6, pp. 462-466.
Schmidt et al., Self-Sealing, Sutureless Scleotomy in Pars-Plana Vitrectomy, 1999, pp. 247-251.
International Search Report dated Nov. 17, 2010 for International Application No. PCT/US2010/049722.

* cited by examiner

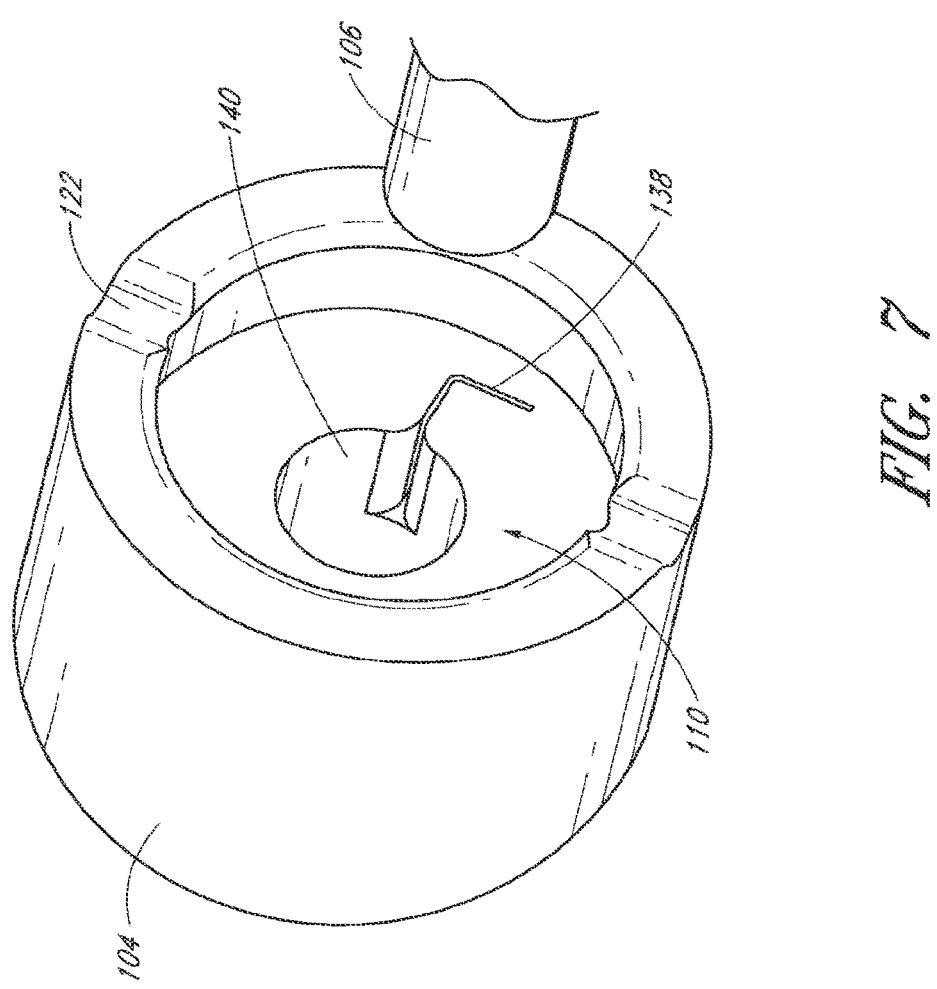

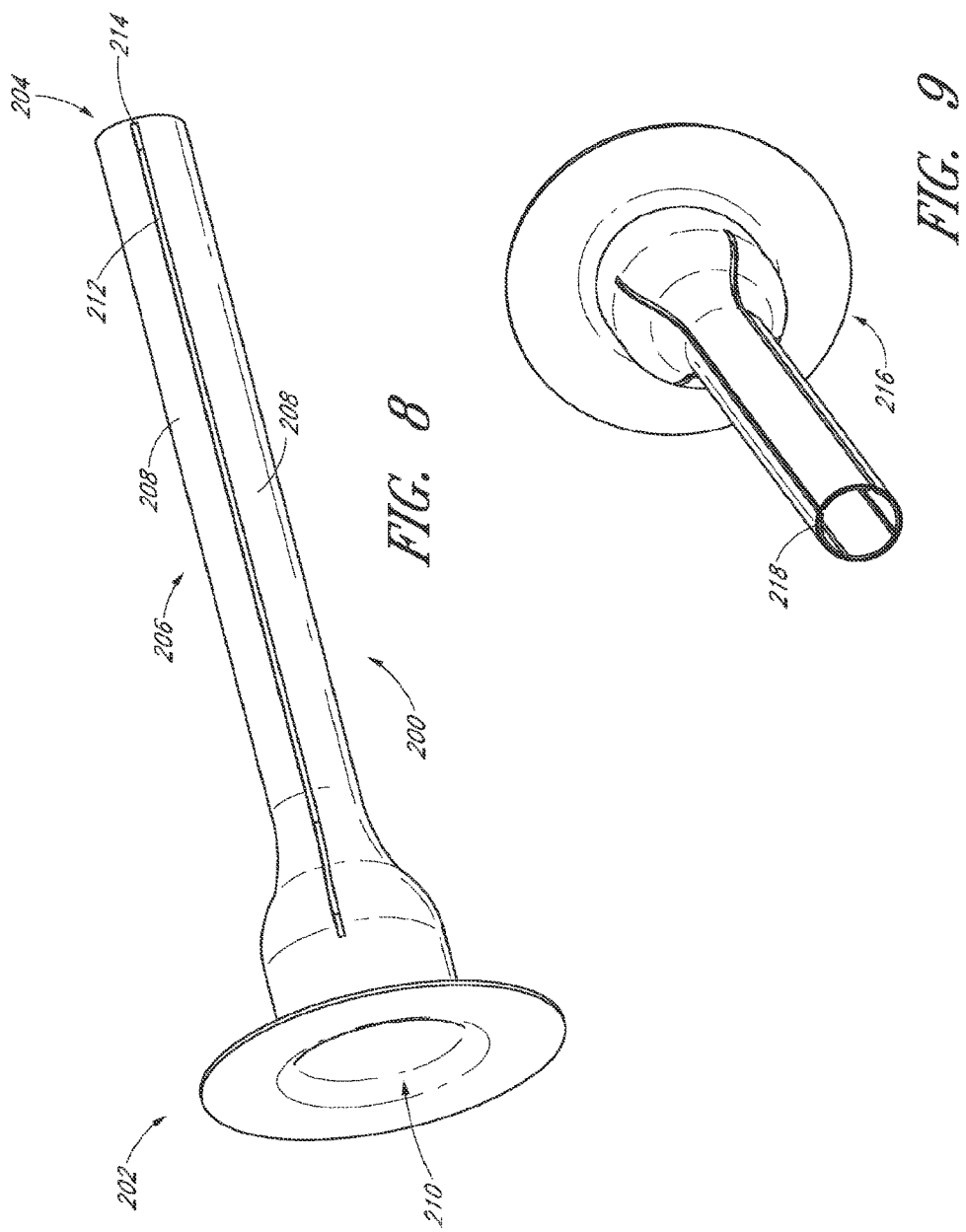

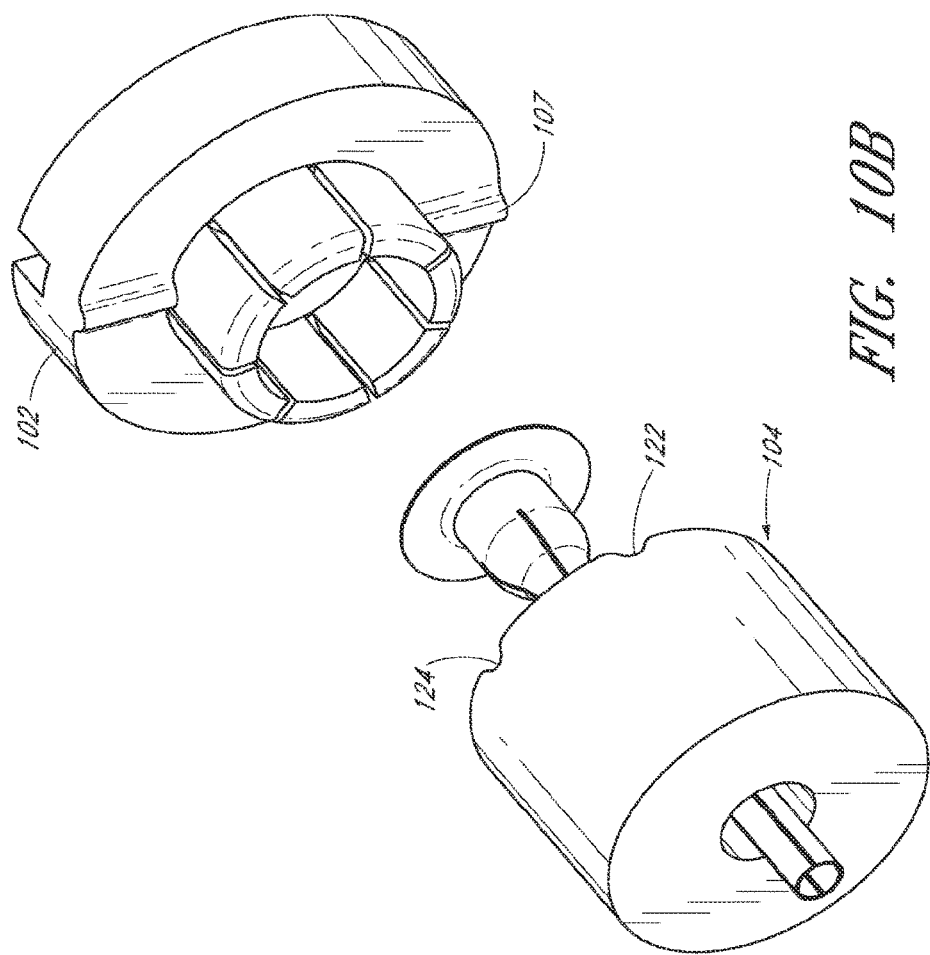

ADJUSTABLE CANNULA SYSTEMS AND DEVICES

The present application is a continuation of U.S. patent application Ser. No. 13/394,467 filed Mar. 6, 2012; which is a U.S. National Application of PCT/US10/49722 filed Sep. 21, 2010; which claims priority under 35 U.S.C. § 119(e) to U.S. Provisional Patent Application Ser. No. 61/244,841, entitled "Adjustable Universal Cannula Systems and Devices," filed Sep. 22, 2009. The entire disclosure of the priority applications are hereby expressly incorporated by reference in its entirety.

BACKGROUND

Field

Embodiments of the invention relate to cannulas and trocars and, in particular, to devices, systems, and methods for adjusting opening sizes of cannulas.

Description of the Related Art

Cannulas typically are tubes inserted into a body part for allowing insertion of fluids, materials, or instruments through the cannula or to allow the drainage or removal of fluids.

The smaller in cross-section that a cannula is, the less trauma is caused to the tissue surrounding the cannula. Recent developments in ophthalmology provide a good example of the benefits of small diameter cannulas. It has become increasingly common for vitreoretinal surgery to use cannulas sized small enough to pass instruments of 23 gauge (ga.) or less through the cannula. This then allows the incision from the cannula site to be small enough to self-seal without having to use sutures. This self-sealing of the incision in-turn allows the cannula to be inserted transconjunctivally, saving time and eliminating the need to incise and retract the conjunctiva before incising the sclera, as required using 20 ga. or larger instruments. While the use of smaller sized cannulas has been beneficial, the necessity of using smaller sized instruments has reduced the efficiency of some aspects of surgery compared to the older standard of using 20 ga. instruments. For example, the use of a vitreous cutter with a 23 ga. or smaller outer diameter takes more time to remove vitreous compared to a 20 ga. outer diameter cutter. Also, the insertion of viscoelastic material through a 23 ga. or smaller lumen is more difficult and time consuming compared to using a 20 ga. lumen. Therefore, it would be desirable to have a cannula system that provides the small incision advantages of a self-sealing incision while still allowing the use of more efficient larger diameter instruments.

Certain aspects, advantages, and novel features of the invention are described in this disclosure. It should be understood that not all possible aspects, advantages, and features may be employed or achieved in accordance with any particular embodiment of the invention.

SUMMARY

Systems and methods related to an adjustable cannula are provided. In some embodiments, an adjustable cannula system for performing eye surgery is provided. The system comprises a bottom housing for placement on an eye, the bottom housing comprising first and second lumens. The system further comprises an expandable member configured to increase and decrease from one diameter to another, the expandable member to be received in the first and second lumens of the bottom housing. The expandable member includes a distal end for insertion into the eye. At least two coupling elements are located at a proximal end of the expandable member. The bottom housing is configured to engage one of the coupling elements, while the top housing is configured to engage the other of the two coupling elements. The diameter of the expandable member can be controlled by rotating the top housing relative to the bottom housing.

In some embodiments, a cannula system is provided that includes an expandable member formed as a coil that increase and decreases from one diameter to another. The cannula system further includes a bottom housing for coupling to and receiving the expandable member including a lumen defining a maximum diameter and a top housing for coupling to the expandable member and to the bottom housing. Coupling of the top and bottom housings forms a detent mechanism providing and maintaining a plurality of expandable member diameters when the top housing is rotated relative to the bottom housing.

In some embodiments, a cannula system is provided comprising an expandable tube having a first tab and a second tab. A bottom housing is coupled to the expandable tube via the first tab and a top housing is coupled to the expandable tube via the second tab, wherein rotation of the top housing relative to the bottom housing results in expansion or contraction of the expandable tube.

In some embodiments, an adjustable cannula is provided comprising an elongate body having a distal end and a proximal end, wherein the proximal end has a lumen larger than a distal end lumen. A plurality of flanges are formed in the elongate body by a plurality of slits spanning a majority of a length of the elongate body. Material is formed between the flanges at the distal end for maintaining an initial minimum diameter of the distal end lumen.

In some embodiments, an adjustable cannula is provided comprising an elongate body having a distal end and a proximal end, the proximal end having a lumen larger than a distal end lumen. A plurality of flanges is formed in the elongate body by a plurality of slits spanning a majority of a length of the elongate body.

In some embodiments, an adjustable cannula comprises an elongate body having a distal end and a proximal end, the proximal end having a lumen larger than a distal end lumen. A plurality of flanges is formed in the elongate body by a plurality of slits spanning a majority of a length of the elongate body. Material is formed between the flanges and substantially fills the slits. The material defines an initial minimum diameter of the cannula, wherein the material has an initial small cross-sectional width upon insertion into tissue and expands to a subsequent larger cross-sectional width at some time after insertion into the tissue so that a working channel of the cannula is enlarged by the material expanding and causing the flanges to separate.

In some embodiments, a cannula system anchored in the pars plana of an eyeball is provided comprising an expandable member that increases and decreases from one gauge to another by electroactive action.

In some embodiments, an adjustable cannula system is provided comprising an elongate body having a proximal portion and a distal portion, wherein an inner diameter of the proximal portion is greater than an inner diameter of the distal portion. A plurality of slits extend from the proximal portion to the distal portion, wherein the slits are configured to accommodate expansion and contraction of the elongate body.

BRIEF DESCRIPTION OF THE DRAWINGS

The features, aspects, and advantages of the inventions are described with reference to the drawings of various embodiments, which are intended to illustrate and not to limit the inventions. The figures are merely illustrative and may not represent the actual scale and size of the device or systems.

FIG. 7 is a perspective of another portion of the cannula of FIG. 2;

FIG. 8 is a perspective view of yet another example of a cannula in accordance with the present invention;

FIG. 9 is another perspective of the cannula of FIG. 8;

FIGS. 10A and 10B are exploded perspectives of still yet another example of a cannula in accordance with the present invention;

DETAILED DESCRIPTION OF THE EMBODIMENTS

Figure 1:
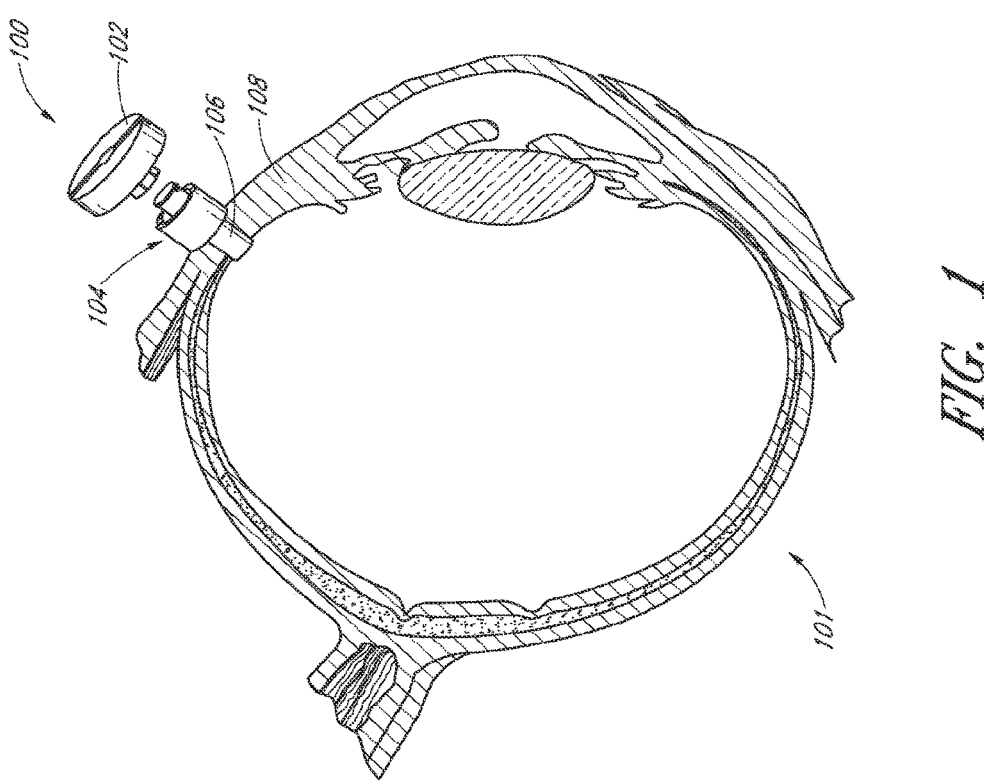
FIG. 1 is a cross-section of an eye including a perspective of a cannula in accordance with the present invention.

Although several embodiments are disclosed, it will be understood that the invention described may extend beyond the specifically disclosed embodiments and includes other uses of the invention and obvious modifications and equivalents. Embodiments of the invention are described with reference to the accompanying figures, wherein like numerals refer to like elements throughout. The terminology used in the following description is not to be interpreted in any limited or restrictive manner. In addition, embodiments of the invention may comprise multiple novel features with no single feature solely responsible for its desirable attributes or essential to practicing the inventions described.

The term "cannula" as used is a broad term, and unless otherwise indicated, may mean, without limitation, a tube, coil, hose, or the like for insertion into a body part. The term cannula may also encompass devices with or without trocars or devices where the cannula itself also functions as a trocar to create in incision. Cannulas can be used to deliver or remove fluids, gases, drugs, materials, oils, tissues, instruments, samples, devices, or the like to and from the body. The diameter of cannulas can be increased, decreased, expanded, or collapsed. Such adjustments of the cannulas can be performed mechanically, thermodynamically, or by using electrical current. Cannulas can be constructed of any suitable material. For example, metals such as nitinol, stainless steel, or the like, or the cannulas can be formed of various plastics or polymers such as polyamide, parylene, or polyurethane.

The embodiments disclosed herein relate to an adjustable cannula. In certain embodiments, the adjustable cannula provides an adjustable port opening enabling surgical procedures in various parts of the body. In some embodiments, the adjustable cannula can be configured to have a small initial diameter, thereby allowing the adjustable cannula to be inserted into small incisions in the body. During the surgery, the surgeon can expand the cross-section or diameter of the adjustable cannula to increase the working channel. In some embodiments, the adjustable cannula can be used in tissue having an elastic, flexible, or resilient characteristic, thus advantageously allowing the diameter of the adjustable cannula to expand and permitting the tissue to return to the approximate size of the initial small incision and self-seal without the need for sutures. By removing the need for sutures, patient discomfort is reduced and/or the risk of infection is decreased. In the case of orthopedic surgeries or other surgeries, a reduced initial surgical opening can minimize scaring and/or decrease the amount of healing time as well as the risk of infection.

In certain embodiments, the adjustable cannula can be used in the technology fields of orthopedics, ophthalmology, neurosurgery as well as other technology fields. The adjustable cannula can be universal, such that is can be applied to many different technologies. In certain embodiments, the adjustable cannula can have diameter range of 3 mm-9 mm in the orthopedics field. In certain embodiments, the adjustable cannula can have diameter range of 0.4-1 mm in the ophthalmic field. In certain embodiments, the adjustable cannula can have diameter range of 1 mm-4 mm in the neurosurgery and orthopedic fields.

FIG. 1 shows an adjustable cannula 100, in accordance with the present invention, and in use in an eye 101. For example, the adjustable cannula 100 can be placed transconjunctivally through the sclera 108, as shown, to provide a port opening for placing, inserting and removing, injecting and aspirating, surgical instruments, fluids, gases, or the like. Adjustable cannula 100 may include a top housing or hub 102, a bottom housing or hub 104, and an expandable member or tube 106. In FIG. 1 and certain other embodiments, the expandable member is in the form of a cylindrical tube (or other conduit with a lumen there through) having a diameter; however, one skilled in the art will appreciate that the expandable member 106 can assume other forms, including non-tubular (e.g., square, oval, asymmetrical, conical) forms.

Generally, in eye surgery the surgeon makes an incision in the eye using a separate knife (not shown) and then inserts a cannula into the incision or inserts a cannula simultaneously with an incising trocar (also not shown) inserted in and extending through the cannula. Depending on the size of the incision, sutures may be required to close and seal the incision after completing surgery. Incisions 20 ga. or larger generally require sutures to close and seal the incision. The use of sutures may cause complications, for example, suture irritation, inflammation, post-operative astigmatism, scleral pigment changes, or the like. Accordingly, some surgeons prefer self-sealing sutureless techniques, for example, making small incisions and inserting a 23, 24, 25 ga., or smaller cannula or port into the eye. Typically, incisions of 23, 24, 25 ga., or smaller allow the incision to self-seal or substantially self-seal after the operation and therefore does not require the use of sutures. However, the use of cannulas or ports having a size of 23, 24, 25 ga., or smaller can affect the efficiency and/or efficacy of the surgery. For example, it generally takes more effort and time to inject gas and fluid (for example, silicone oil) through a 23, 24, or 25 ga. port compared to a 20 ga. port. Additionally, surgeons are limited in the types and sizes of instruments that can be used during surgery using 23 ga. or smaller instruments compared to the older traditional 20 ga. instruments. For example, surgeons cannot insert as large of a light instrument through a 23 ga. or smaller port compared to a 20 ga. port, thereby possibly impeding the surgeon's ability to illuminate and visualize the posterior chamber of the eye.

In some embodiments, an adjustable cannula 100 is provided. In some embodiments, the adjustable cannula 100 includes an expandable member 106 in the form of a tube that is in part cylindrical with a diameter, while in other embodiments, the expandable member 106 can assume other forms without a diameter, while still being expandable and contractible. In some embodiments, the adjustable cannula 100, as disclosed, may have a small initial diameter for use as a 23, 24, 25 ga., or smaller port, and, advantageously, the surgeon can expand the diameter of the adjustable cannula 100 to increase the working channel to potentially accommodate a 20 ga. or larger instrument. Accordingly, the adjustable cannula system, as disclosed, allows surgeons to make smaller incisions in the body without sacrificing the greater efficiency of a larger diameter size of the working channel. The resilient, elastic nature of the tissue allows the tissue to return to approximately its initial small self-sealing size after removal of the adjustable cannula 100, despite the cannula 100 having expanded the initial incision to accommodate a larger working channel. In some embodiments, while the adjustable cannula 100 displaces or stretches some surrounding tissue during use, after contracting and/or removing the adjustable cannula 100 from the patient, tissue can return to approximately near or at their original position prior to displacement or stretching by the cannula.

In certain embodiments, a surgeon may initially insert an expandable tube 106 sized to accommodate a 23, 25, 27, 28 ga. or smaller port in the eye. During surgery, the surgeon can increase the diameter of the expandable tube 106 by attaching top housing 102 to the expandable tube 106, seating the top housing 102 in the bottom housing 104, attaching the expandable tube 106 to the bottom housing 104, and rotating the top housing 102 relative to the bottom housing 104 causing the expandable tube 106 to a least partially uncoil, creating a larger working channel. In certain embodiments, the diameter of the expandable tube 106 can be increased to 27, 26, 25, 24, 23, 23, 22, 21, 20, 19, 18 ga. (0.4-1 mm), or larger. In some embodiments, the diameter of the tube 106 can be expanded from a first position to a second position by between about 1% and 80%, or between about 20% and 40%.

Figure 2:
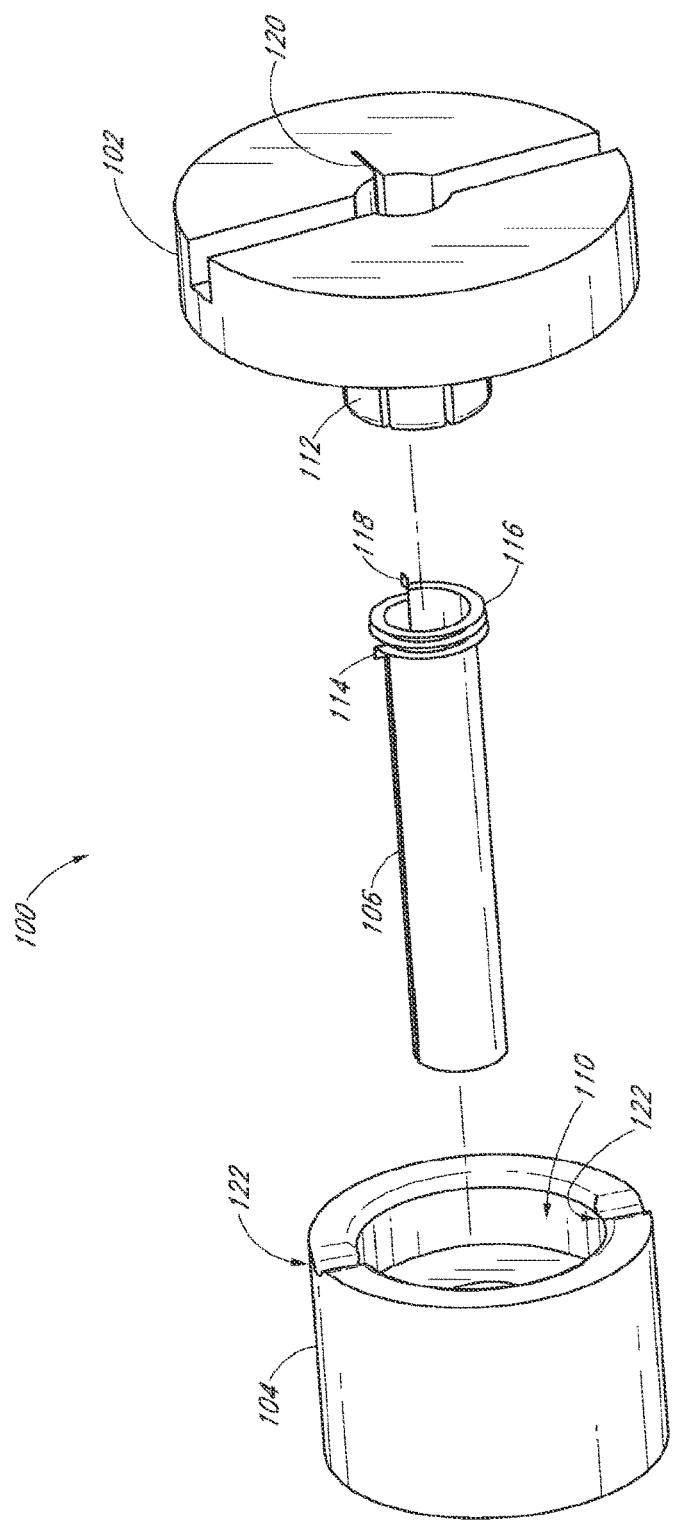
FIG. 2 is an exploded perspective of the cannula of FIG. 1.

FIG. 2 shows the adjustable cannula 100 of FIG. 1 in exploded perspective. Bottom housing 104 includes a first lumen 110, through which tube 106 passes and in which locking mechanism 112 is rotatably received. Bottom housing 104 also includes a second smaller lumen (shown below) through which tube 106 is inserted and a slot (also shown below) for coupling with coupling element 114 of tube 106. While the coupling element 114 is in the form of a tab or protrusion, the coupling element is not limited to these particular shapes or forms. The flange or lip 116 helps to retain the tube 106 in bottom housing 104. The coupling element 118 of tube 106 couples with the top housing 102 via slot 120. Like coupling element 114, while coupling element 118 is in the form of a tab or protrusion, the coupling element is not limited to these particular shapes or forms. When fully assembled, a user rotating top housing 102 in a clockwise direction while holding bottom housing 104 stationary or rotating bottom housing in a counterclockwise direction causes expandable tube 106 to expand. In other embodiments, the components can be configured such that the top housing 102 can be rotated in a counterclockwise direction to cause expandable tube 106 to expand. Preferably, locking mechanism 112 has a slight taper that mates with a taper of lumen 110 so that top housing 102 is snuggly and rotatably coupled to bottom housing 104. A snap-fit using detents or the like (not shown), as known by those skilled in the art, may also be used to ensure that top housing 102 stays coupled to bottom housing 104 yet allows for rotation. Top housing 102 includes a protrusion (shown below) that matingly seats with notches 122, essentially forming a detent mechanism to hold expandable tube 106 at a desired diameter. The coupling of the top and bottom housings 102 and 104 forms a detent mechanism providing and maintaining a plurality of expandable tube 106 diameters when the top housing 102 is rotated relative to the bottom housing 104.

Expandable tube 106 is preferably made at least in part of a thin, resilient material such as nitinol (a memory metal) or other shape memory alloy (e.g., Cu—Al—Ni), stainless steel, or other suitable material that can form a sufficiently small diameter coil and yet be robust enough not to collapse against the pressure of stretched tissue. In some embodiments, the tube 106 can be composed of a plastic with metal (e.g., nitinol) pieces embedded therein. In some embodiments, having the exposed portion of the cannula formed of plastic advantageously minimizes the risk of harm to surrounding tissue caused during expansion, as plastic is more deformable relative to metal and does not apply the same degree of force in multiple directions as metal. In some embodiments, the materials can be biocompatible, or can be provided with a protective layer (e.g., of aluminum oxide) to enhance biocompatibility. In some embodiments, the expandable tube 106 can be formed in part of a material that has an elasticity of between $20 \times 10^6$ psi and $2 \times 10^6$ psi that allows the expandable tube 106 to return to an original, non-expanded state with ease. Such elastic material advantageously allows the expandable tube 106 to be used multiple times in different surgical operations, without having concern about long-term deformation.

In some embodiments involving an adjustable cannula 100 with an expandable coil, the coil can cooperate with tissue to assist in sealing the interior of the cannula (e.g., such as when the coil is expanded). To minimize the risk of tissue and other materials from becoming captured in the expanded coil, the edges of the coil can be slanted toward the interior portion of the coil, thereby allowing tissue to slide off the slanted edges and away from the interior portion of the coil during coil expansion or contraction. In addition, in some embodiments, the coil can be provided with a biocompatible coating that reduces the friction between coil and the tissue/other materials, thereby reducing the risk of capturing tissue and other materials by the coil. The surface of the coil can be substantially smooth to allow tissue and other materials to slide off the coil, thereby preventing tissue or materials from being captured by the coil. In an embodiment, the coil is substantially tightly wound to reduce the amount of the space between layers of the coil, thereby preventing tissue and other materials from becoming captured by the coil.

Figure 3:
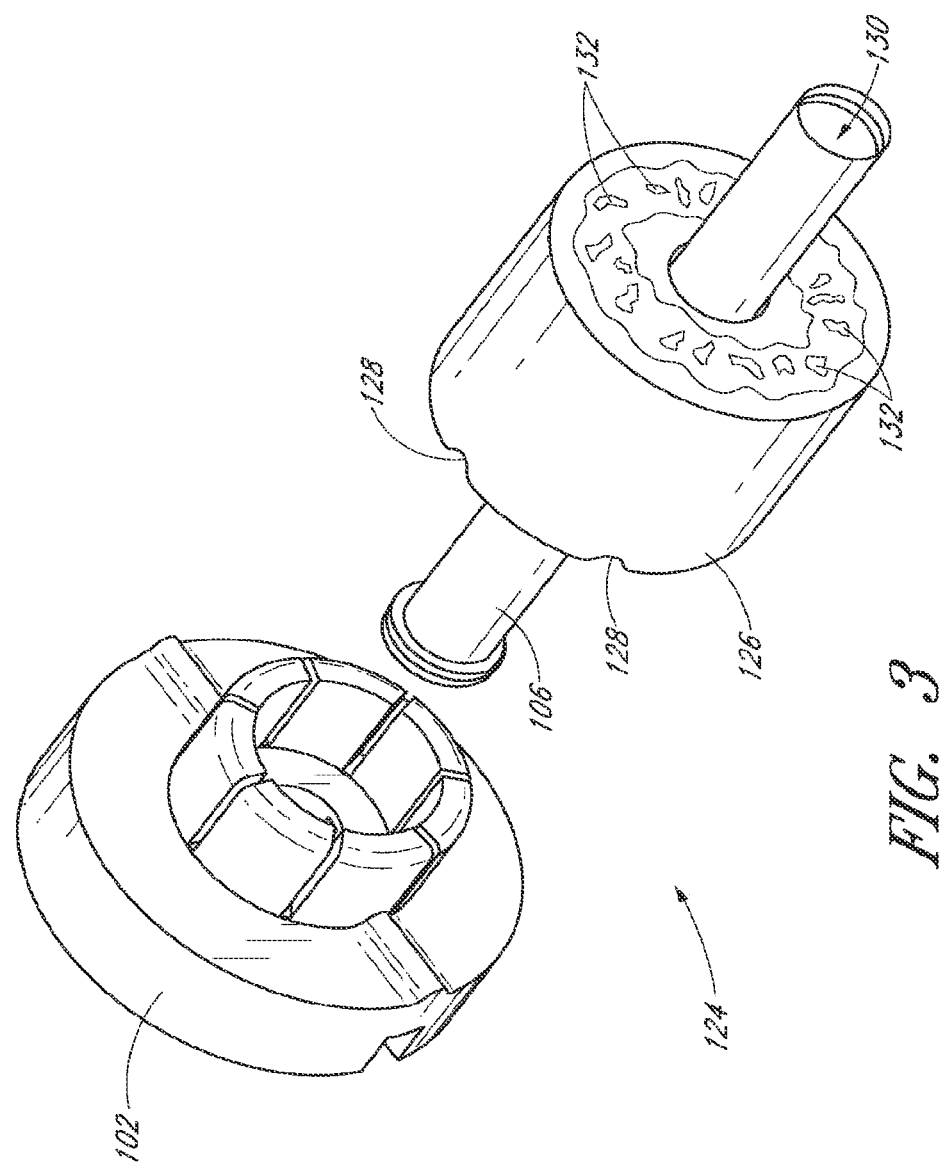
FIG. 3 is a partially assembled view of another example of a cannula in accordance with the present invention.

FIG. 3 is a partially exploded perspective of another example of an adjustable cannula 124. Adjustable cannula 124 is essentially the same as the example shown in FIG. 2, except that bottom housing 126 has more notches 128 for more selectivity regarding the lumen 103 diameter of tube 106. Additionally, bottom housing 126 has several barbs 132 for grabbing tissue to facilitate rotation of top housing 102 with respect to bottom housing 126 and thus, adjustment of the lumen diameter 130 of expandable tube 106. In some embodiments, the barbs 132 are formed and integrated with the bottom housing 126, while in other embodiments, the barbs 132 are removably coupled to the bottom housing 126 such that they can be removed if desired.

Figure 4:
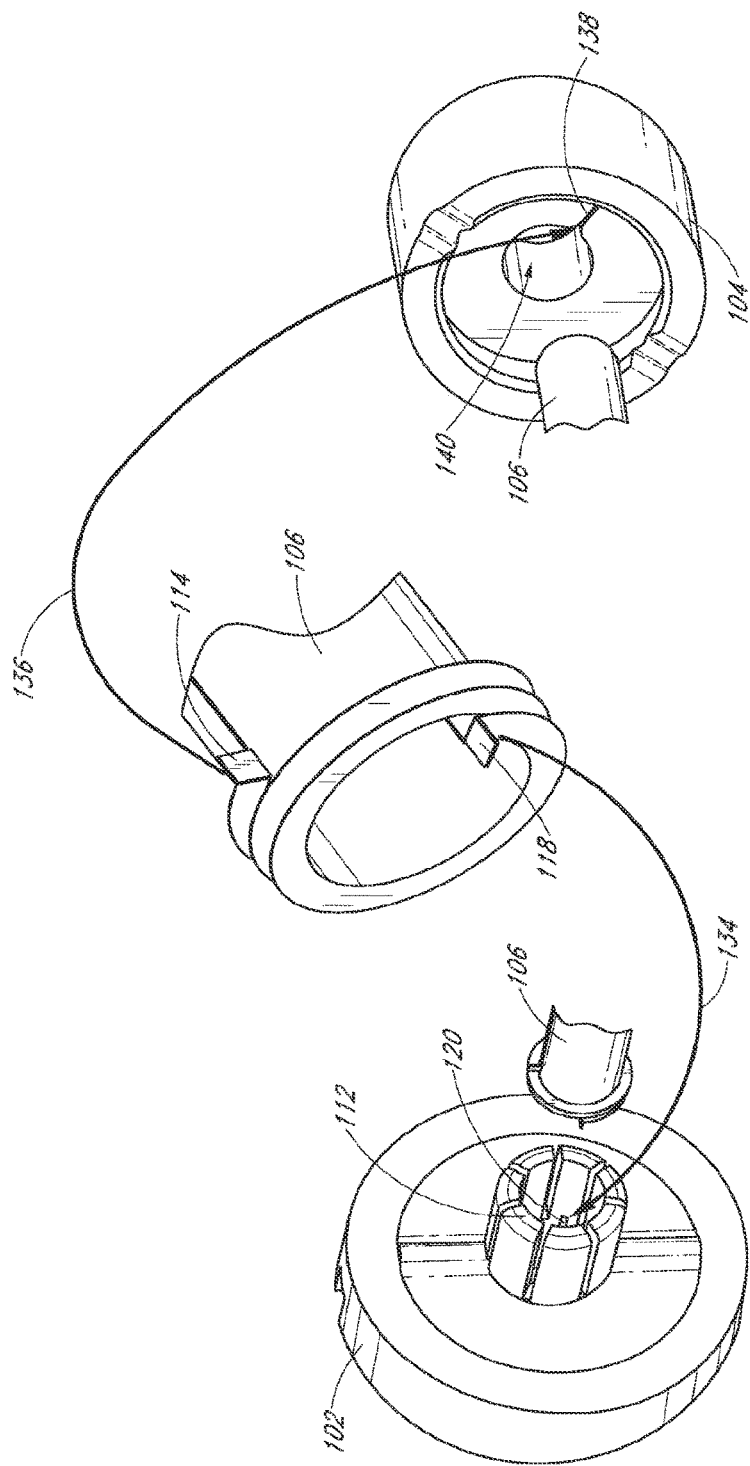
FIG. 4 is a partial exploded view of the cannula of FIG. 2.

FIG. 4 is a partial exploded perspective of the embodiment of FIG. 2, showing the coupling of expandable tube 106 to the top and bottom housings 102 and 104. Tab 118 of the expandable tube 106 fits into slot 120 of the top housing 102 as shown by arrow 134. Arrow 136 shows tab 114 of the expandable tube 106 fitting into slot 138 of the bottom housing 104. Accordingly, in some embodiments, the bottom housing 104 is coupled to the expandable tube 106 via a first tab 114, while the top housing 102 is coupled to the expandable tube via a second tab 118. Rotation of the top housing 102 relative to the bottom housing 104 results in expansion or contraction of the expandable tube 106.

The view in FIG. 4 also shows the second smaller lumen 140 of bottom housing 104. The second lumen 140 receives the expandable tube 106. Advantageously the second lumen 140 may be configured to limit a maximum diameter size to which the tube 106 can be expanded. By so limiting, second lumen 140 is a safety mechanism preventing the expandable tube 106 from expanding too much and damaging or tearing the surrounding tissue. For example, the second lumen 140 can be sized to limit the tube 106 from expanding beyond accommodating a 20 ga. instrument and protect the sclera from tearing or other damage. In other areas of the body, the second lumen 140 can be configured to limit the tube 106 from expanding beyond a maximum design limit (example 4 mm) to prevent surrounding tissue from tearing, or becoming damaged.

Figure 5:
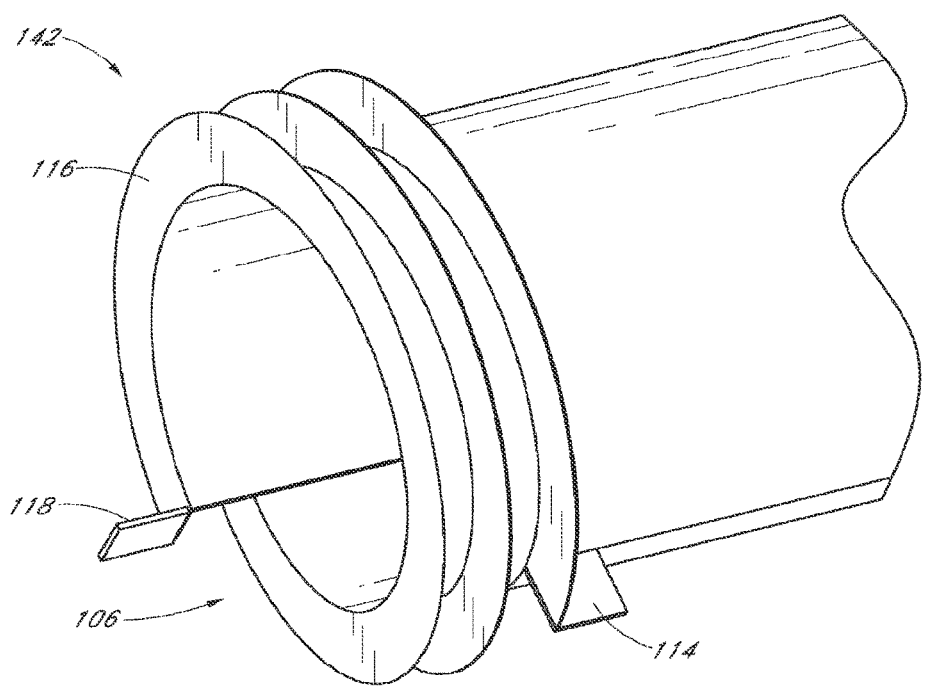
FIG. 5 is a partial perspective of the cannula of FIG. 2.

In certain embodiments, the expandable tube 106, shown in partial perspective in FIG. 5, is a coiled or a wound-up material. The expandable tube 106 can be constructed of metal (for example, nitinol), a plastic, or a polymer, or combination thereof. The thickness of the tube 106 material can be about 0.001 inches (0.0254 mm), and can range from about 0.001 inches (0.0254 mm) to about 0.01 inches (0.254 mm). In some embodiments, the expandable tube 106 can have a length of between 3 mm and 15 mm. The expandable tube 106 comprises a distal end (shown in above figures) for insertion into the eye, and a proximal end 142 which preferably remains external to the eye during use. Flange 116 prevents tube 106 from passing through lumen 140, shown in FIG. 4.

Figure 6:
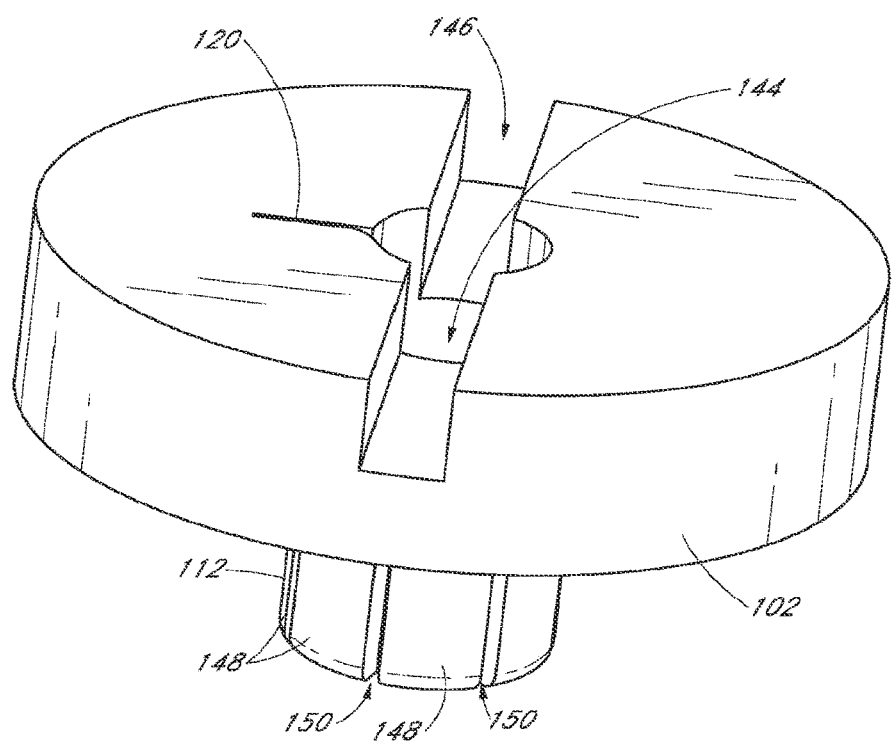
FIG. 6 is a perspective of a portion of the cannula of FIG. 2.

FIG. 6 is a perspective view of top housing 102 showing attachment mechanism 112, slot 120, and lumen 144. Lumen 144 receives instruments and materials to be inserted into or removed from the eye and communicates with lumen 140 of tube 106. Instruments can include, for example, biopsy devices, scissors, tissue cutting and/or removal devices, draining devices, endoilluminators, fluid infusion devices, and the other surgical instruments. A groove 146 spans the diameter of top housing 102. In some embodiments, an instrument having a mating end can be inserted into the groove 146 and can assist in clockwise or counter-clockwise rotation of the top housing 102.

FIG. 7 is a perspective of bottom housing 104 clearly showing first lumen 110, second lumen 140, notches 122 and slot 138 for coupling with tab 114. From this angle, the notches 122 are shown as grooves along the perimeter of the cannula. Also from this angle, it is shown that in some embodiments the slot 138 can be curved or angled. This design of the slot 138 advantageously helps to secure a tab member 114 within the bottom housing 104.

Thus as has been described above, an adjustable cannula, in accordance with the present invention, the user can rotate the top housing 102, which engages tab 118 causing the expandable tube 106 to also rotate with respect to bottom housing 104. Depending on the direction of the rotation, the expandable tube 106 either coils or uncoils causing the lumen 140 diameter of the expandable tube 106 to decrease or increase. The coiling or uncoiling can occur because the tab 118 is held fixed or substantially fixed or in position through engagement with the bottom housing 104. In certain embodiments, bottom housing 104 may be anchored to tissue or held by the physician to allow the relative rotation of top housing 102. With the tab 118 rotating while the tab 114 is fixed or substantially fixed, the expandable tube 106 is increased or decreased in diameter, thereby increasing or decreasing the diameter of the working channel, i.e. lumen 140. In certain embodiments, the expandable tube 106 is configured to uniformly expand and contract or substantially uniformly expand and contract at the proximal end and the distal end, as the user rotates the top housing 102. In other embodiments, the expansion and contraction of proximal end 142 may be greater than the expansion and contraction of the distal end of tube 106. The expandable tube 106 may be extracted after reducing the expandable tube 106 to a smaller diameter, preferably as small as possible to minimize trauma to surrounding tissue during extraction.

In certain embodiments, the locking mechanism 112, shown in FIG. 6, can engage the lower housing element 104 to lock the top housing 102 in a user selected position and maintain a particular diameter of the expandable tube 106. The locking mechanism 112 can comprise flexible fingers 148 extending distally and with spacing 150 between each finger 148. In certain embodiments, the distal ends of the fingers 148 are configured to taper or push outward so as to exert a radial outward force against the inner surface of bottom housing 104 defining lumen 110 to engage the top housing 102 with the bottom housing 104 and retain the top housing 102 connected with the bottom housing element 104. In certain embodiments, lumen 110 is partially conical or tapers. Said another way, the lumen 110 has a wider distal end (larger diameter) and a narrower proximal end (smaller diameter). In certain embodiments, the fingers 148 form a partially conical shape, i.e. the fingers 148 form a wider distal region (larger diameter) and narrower proximal region (smaller diameter). In certain embodiments, the user may pull the top housing 102 proximally outward or away from the bottom housing 104 causing the flexible fingers 148 to be pushed inward as the flexible fingers 148 are forced into the narrower portions of the lumen 110. When the top housing 102 is released by the user, the resilient force of the flexible fingers 148 pushes the fingers 148 distally inward into the lumen 110, allowing the flanges to return to a more relaxed state.

FIG. 8 discloses another example of an adjustable cannula 200 where cannula 200 is an elongate body with a proximal end 202, a distal end 204, and a middle region 206 between the proximal and distal ends. As can be seen, there is no particular structure delineating the proximal end 202 from the middle region 206 or the middle region 206 from the distal end 204. The terms proximal end, middle region, and distal end are intended to refer to the general areas of the cannula 200 and not to a specific spot or place on cannula 200. The initial diameter of the adjustable cannula 200 at the proximal end 202 can be larger than the initial diameter of the cannula 200 at the distal end 204 and the middle region 206. In certain embodiments, the distal end 204 and the middle region 206 are formed by elongated flanges 208 configured to flex when an object, fluid, gas, tissue, device, or the like is inserted through the lumen 210. As the flanges 208 flex, the working channel or diameter of cannula 200 increases and decreases. Sufficient force of the flanges 208 pressing against the resilient elastic surrounding tissue allows the increase of the working channel. Conversely, when the compressive force of the resilient elastic surrounding tissue presses against the flanges 208 is greater than the force exerted by the cannula, the working channel will decrease, i.e. the diameter of cannula 200 will decrease. In some embodiments, an instrument (e.g., such as a probe) can be provided within the cannula that retains expansion of the cannula even against pressure from the tissue.

In some embodiments, the flanges 208 of the cannula 200 are separated by slits 212. The slits 212 of the cannula 200 can cooperate with surrounding tissue to assist in sealing or maintaining closure of the interior of the cannula 200. Upon expansion of the cannula walls, the slits 212 of the cannula also expand, such that the openings of the slits 212 can increase. While the increase in size of the slits 212 can expose the interior lumen of the cannula 200, such that material (e.g., liquid) within the cannula can leak, the slits 212 of the cannula 200 can advantageously cooperate with the surrounding tissue to thereby maintain closure of the interior lumen of the cannula. The tissue, which is generally elastic, can advantageously occupy all or a portion of the spaces in the openings of the slits, thereby providing a blocking function by serving as the "walls" of the cannula. Accordingly, liquid in the cannula can be inhibited from leaking out due to the blocking tissue, even when the cannula 200 is expanded.

In the illustrated embodiment, the cannula 200 comprises two or more slits 212, such as three, four, five, six, seven or eight slits. In other embodiments, the cannula 200 comprises a single slit such that the cannula is "C-shaped." The number of slits 212 can affect the performance of the cannula in transporting fluids and tissue. For example, a fewer number of slits can result in the slit openings or the gap size of the slits being larger in size during cannula expansion, which can result in tissue being inadvertently captured in the slit openings during contraction following expansion such that the slits remain open.

Generally, an expanded cannula with fewer slits, can increase the gap size of the slits may increase, thereby increasing the chances of capturing or catching tissue or other unwanted material in the slits while the cannula is contracting. While increasing the number of slits may reduce the gap size of the slits, and thus the risk of capturing or catching material in the slits during contraction, the strength or rigidity of the cannula walls may decrease, which is important for preventing collapse of the cannula during insertion. Accordingly, a cannula for insertion may benefit from at least two or three slits and fewer than five or six slits. However, in other embodiments, the number of slit can range from 2-10, or 1-20, or 1-25. One skilled in the art will realize however that providing a cannula with at least one slit can provide numerous advantages over conventional cannulas without slits.

The one or more slits 212 advantageously accommodate and modulate expansion and contraction of the cannula. While the expansion and contraction can occur by an electrical, mechanical or magnetic means, in some embodiments, the expansion and contraction are performed mechanically means, by insert of, for example, a probe (as shown in FIG. 15C). The slits can be positioned symmetrically around the cannula (e.g., three slits at a 120 degrees apart) or asymmetrically. In some embodiments, two or more slits can have similar widths, while in other embodiments, two or more slits can be of varying widths. In some embodiments, having slits advantageously allow tissue (e.g., scar tissue as in diabetic retinopathy) or other material (e.g., a foreign body such as a piece of metal during hammering) to be removed from the eye, that has entered the eye.

In other embodiments, the walls of the slits 212 can be configured to allow tissue or other materials to squeezed out or otherwise removed while the walls of the cannula contract from an expanded state. For example, the side walls of the slits 212 can be substantially smooth so as to reduce the risk of catching or capturing tissue or other materials during contraction. In an embodiment, the side walls of a slit 212 can form a substantially wedge shaped configuration to prevent tissue or other materials from being captured in the slits during contraction. The open side of the wedge can face into the interior of the cannula or face outwardly to the exterior of the cannula. The side walls of a slit 212 can be substantially curved or rounded to prevent tissue or other materials from being captured in the slits during contraction. The side walls of the slit 212 can also comprise a coating, for example, Teflon, to prevent tissue or other materials from being captured in the slits during contraction.

An additional advantage of having a cannula 200 with slits 212 is that viscous fluids, which would otherwise be very difficult to push through a small cannula, can be more easily pushed through one with the slits 212, as the slits 212 can open up under pressure of the fluid. For example, infusing 1000 centisoke or 5000 centisoke silicone oil in the eye can result in an opening of the slits when desired. Adding such fluids removes the need to use an instrument or probe to open the slits 212.

In some embodiments, to expand the flanges 208 with slits 212, a mechanical means can be provided to force the expansion. In some embodiments, the mechanical means comprises a probe (as shown in FIG. 15C) that can be inserted into the cannula 200 to expand the flanges 208. The probe can comprise a light source, cutter, diathermy tool, or any other surgical instrument capable of insertion into the cannula 200 and forcing expansion of the cannula 200. Other probes can also include but are not limited to scissors, blades, picks, forceps, and lens removal devices for dropped lens fragments. In operation, when the probe is inserted into a cannula 200 with slits 212, the interior walls of the cannula 200 will expand outward. In some embodiments, the proximal most end of the cannula 200 (which may not include a slit) need not be expandable, and can be set to the maximum probe size available for the procedure. Advantageously, the slits 212 help to mechanically accommodate and modulate the degree of expansion of the cannula 200. Upon removal of the probe, the cannula 200 will contract to a reduced size. Accordingly, the adjustable cannula 200 with slits 212 is user friendly because it requires no forceful mechanical manipulation of the cannula 200 to expand or contract the diameter of the cannula. Further, the adjustable cannula 200 with slits 212 requires no moving parts and thus can be easily manufactured with a single injection molding process.

In some embodiments, one or more probes can be of a single size, such that expansion of the cannula 200 is achieved by using multiple probes that increase in size. For example, in one embodiment, three different probes of various increasing gauges (e.g., 25 ga., 23 ga. and 20 ga.) can be used to assist in the expansion of the cannula. In other embodiments, a probe can be of an adjustable size, such that only a single probe need be used to assist in the expansion of the cannula 200.

In some embodiments, the probe can have a hollow interior to allow for tools or instruments, as well as liquids and tissue, to pass therethrough. In some embodiments, the probe can therefore serve as both an expansion tool for the cannula 200 with slits 212, as well as access port to access a target site.

In certain embodiments, flanges 208 are prevented from separating at their extreme distal ends by material 214. As the extreme distal ends of the adjustable cannula 200 can rest against an eye, preventing separation of the extreme distal ends of the cannula advantageously reduces damages to the eye that can occur during expansion and contraction of other parts of the cannula. Material 214 may be formed of the same material as flanges 208 and molded simultaneously with cannula 200 in manufacture, such that the elongate body is a single unitary molded piece. One skilled in the art will appreciate that material 214 is optional, and that in other embodiments, the cannula may be expandable even at its extreme distal end.

Alternatively, material 214 may be a ring of material placed or attached to flanges 208, as shown in detail below. Material 214 may serve one or more purposes. These purposes include maintaining a small initial diameter of the distal end 204 and middle region 206 as cannula is inserted into tissue by a trocar (not shown) held within cannula 200 and extending beyond distal end 204. Another purpose of material 214 is to allow the flanges to flex and slits 212 to expand under the pressure of viscoelastic being inserted into the eye, thereby effectively enlarging the volume of the cannula 200 in the eye to allow faster and easier injection of viscoelastic. Conversely, when no increased pressure is present the flanges 208 may return to an unflexed state with minimal width slits 212 to assist in preventing fluid escaping the eye.

An alternate purpose of material 214 is to be only robust enough to maintain the initial small diameter during insertion of cannula 200 into tissue but weak enough to break upon the insertion of a device larger in diameter than the initial small diameter. In this way, flanges 208 are allowed to separate from each other and flex or bend outwardly to provide a wider working channel.

Lumen 210 may be large enough to accommodate and define the largest acceptable diameter that flanges 208 are allowed to flex, such as for a 20 ga. or greater vitreous cutter, while the distal end and middle region diameters are small enough to require a minimal sized incision in the tissue, similar to that describe above with respect to expandable tube 106. In some embodiments, slits 212 can extend a substantial length, even a majority of the length, of cannula 200 and at least long enough to allow flanges 208 to separate sufficiently to accommodate the largest diameter device compatible with lumen 210. For example, the slits 212 can extend from a distal end 204 to a wider proximal end 202 of the cannula 200. In other embodiments (not shown), instead of a series of single slits that extend a substantial length of the cannula, a series of multiple slits can extend along a single line and can be provided to accommodate expansion and contraction of the slits.

As can be seen in FIG. 8, in a non-expanded state, a proximal end 202 of the cannula 200 can have a larger diameter than a middle 206 and/or distal end 204 of the cannula. In some embodiments, the proximal end 202 of the cannula 200 remains outside of patient (e.g., outside of an eye) such that it need not be expanded or contracted. Rather, it can be sized larger than the middle 206 and/or distal end 204 of the cannula 200 to thereby facilitate the insertion of instruments into the cannula, and provide greater visual access to a surgeon utilizing the cannula. For example, for instruments insertable into the cannula 200 that may have a broader proximal portion (e.g., a handle portion) than a distal portion, the broader proximal portion of the instrument can be inserted with ease into the broader proximal end 2020 of the cannula 200. After expansion of the cannula 200, the middle 206 and/or distal end 204 can be less than, the same as, or greater than the diameter of the proximal end 202 of the cannula 200.

In embodiments involving a cannula 200 with slits 212, the cannula 200 can be comprised in part or substantially of a plastic material. In some embodiments, to form the cannula, the plastic can be injection molded, such as in a single shot. Different plastic-based materials can be used to form the cannula 200, including but not limited to organic and synthetic polymers, polyamide (Nylon), polyoxymethylene (Delrin), parylene, and polyurethane. In some embodiments, the cannula 200 can be formed of a plastic-based material that provides sufficient rigidity to the cannula 200, while also maintaining some degree of flexible to accommodate expansion and contraction of the cannula 200 during use. In some embodiments, the cannula 200 can have a Flexural Modulus of between $3\times10^5$ PSI and $5\times10^5$ PSI. In some embodiments, the cannula 200 can be formed of a plastic with metal pieces embedded therein.

FIG. 9 is a perspective of another example of an adjustable cannula 216 in accordance with the present invention. Cannula 216 is essentially the same as cannula 200 except that material 214 is replaced by ring 218. In some embodiments, the ring 218 is removable. Ring 218 may be resilient and expandable or rigid, depending on the purpose of using cannula 216. Ring 218 may be adhered to cannula 216 with an acceptable adhesive or may be held in place by any known attachment mechanism.

Figure 10A:
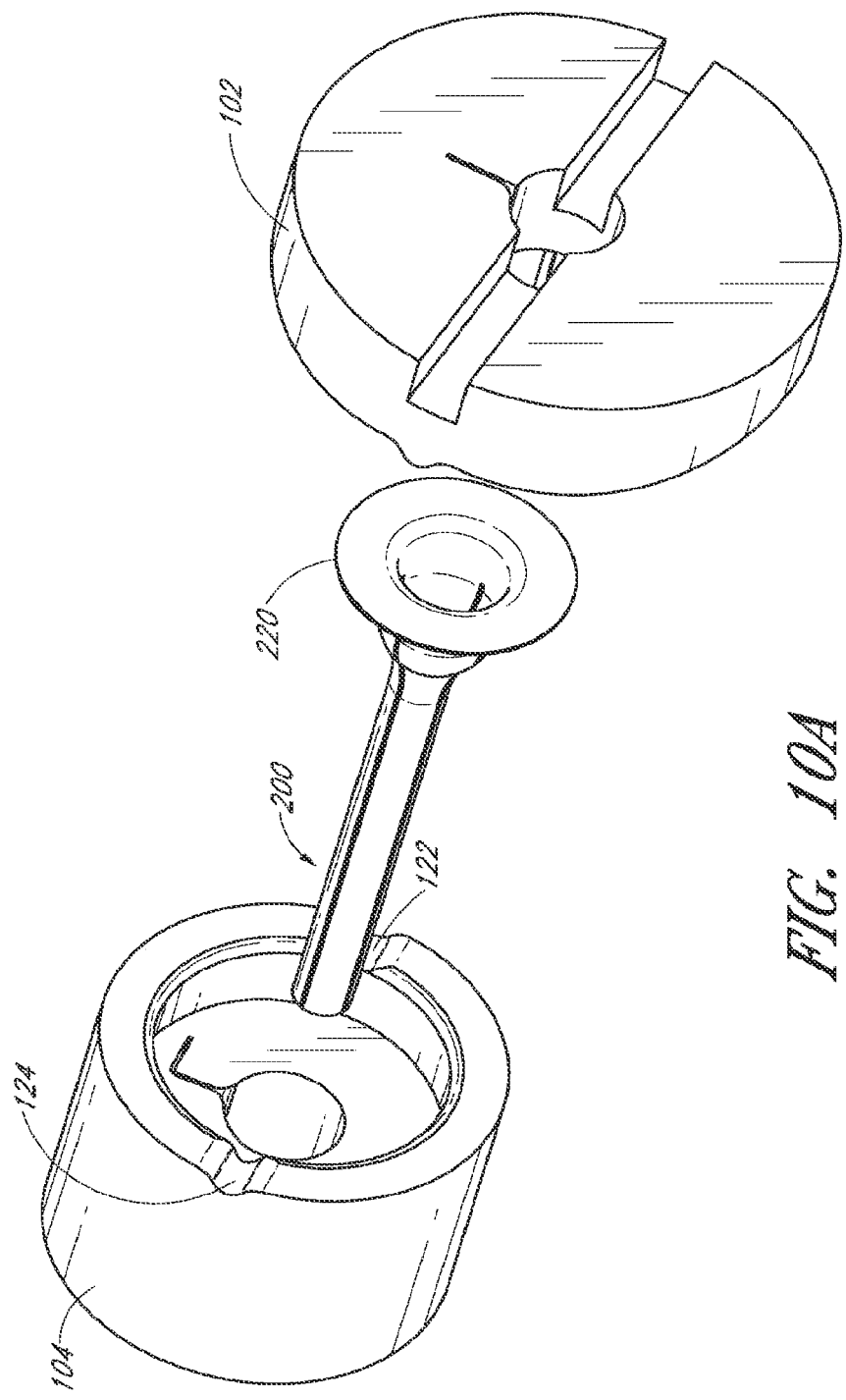

The cannulas 200 and 216 may be used alone with a trocar device, or with top and bottom housings 102 and 104, as shown in FIGS. 10A and 10B. In some embodiments, the top and/or bottom housings 102 and 104 may be used to provide more structure to hold cannulas 200 or 216 in place during surgery. Though slots 120 and 138 are shown, they are not needed for cannulas 200 and 216. Flange or rim 220 is held between bottom housing 104 and the fingers (not shown) of top housing 102.

In FIGS. 10A and 10B, certain features of the top housing 102 and bottom housing 104 are apparent. The top housing 102 comprises at least one ridge element 107 configured to engage a plurality of grooves or notches 122 and 124 in the bottom housing 104. The first and second notches 122 and 124 are sized and configured to securely position at least one ridge element 107. In certain embodiments, the at least one ridge element 107 is configured to fit within notch 122 to lock the top housing 102 into a particular position. In some embodiments, to rotate the top housing 102 to a different position, the user can pull the top housing 102 proximally outward and rotate the top housing 102 to disengage the ridge element 107 from the notch 122 and engage a second notch 124. Upon rotation of the top housing 102, the cannula 200 can expand or contract. Accordingly, the cannula can be securely kept in a first state while the ridge element 107 is in a first notch 122, and securely kept in a second expanded or contracted state relative to the first state while the ridge element 107 is in a second notch 124.

Figure 11:
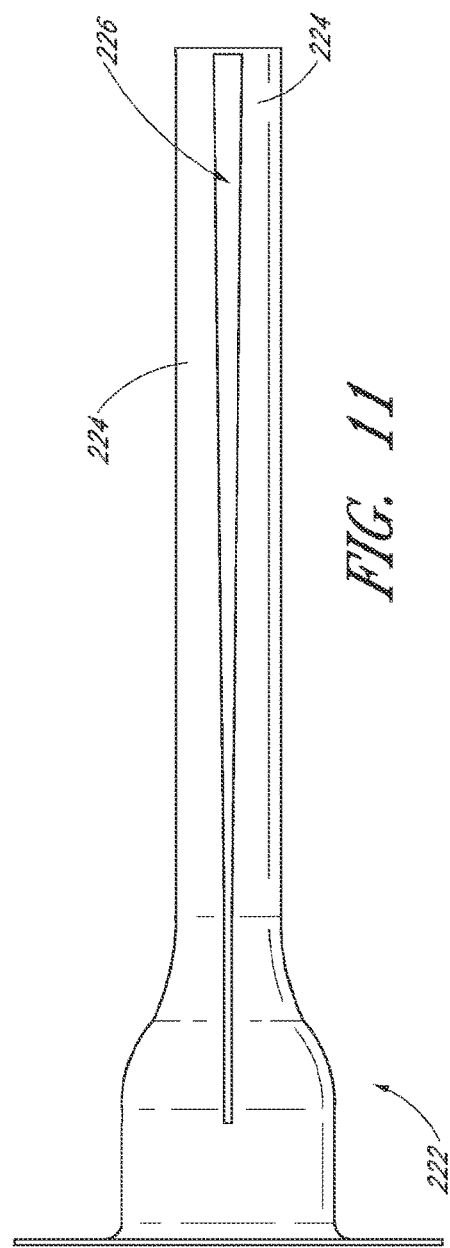
FIG. 11 is an elevation of yet another example of a cannula in accordance with the present invention.

FIG. 11 shows another cannula 222 and differs from cannula 200 in that flanges 224 taper so that slits 226 between flanges 224 progressively widen towards the distal end of cannula 222, thereby advantageously providing for varied expansion along the length of the cannula. For some applications, this configuration of flanges 224 may be advantageous such as providing more space for maneuvering instruments during surgery.

Figure 12:
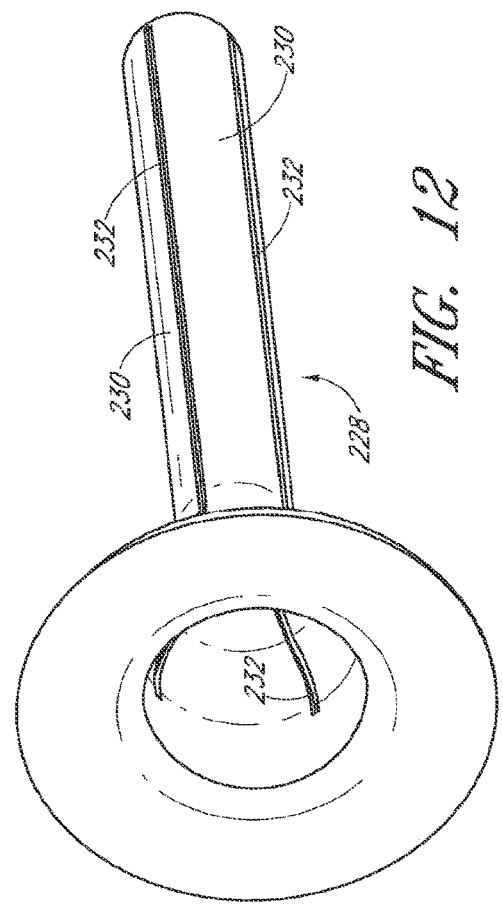
FIG. 12 is a partial perspective of yet another example of a cannula in accordance with the present invention.

FIG. 12 shows yet another cannula 228 having flanges 230 with thermodynamically changing material 232 filling the space between the flanges 230. Material 230 has an initial small cross-sectional width upon insertion into tissue and expands to a subsequent larger cross-sectional width at some time after insertion into tissue so that the working channel of cannula 228 is enlarged by the force of material 230 expanding causing flanges 230 to further separate. Material 230 can be attached between flanges 230 by any known manufacturing techniques including adhesive, molding, injection, etc. Material 230, depending on the amount of expansion and contraction needed, can be any number of materials such as various hydrogels. Material 230 may begin at a low temperature by being quickly treated with a Cryo-device, often used in many surgeries, immediately before insertion and then material 230 may increase in temperature from contact with surrounding tissue and materials being injected and aspirated from the surgical site. As material 230 increases in temperature, material 230 expands. Material 230 may also take the form of hydrophilic materials. Hydrophilic materials absorb moisture and expand as moisture is absorbed and therefore material 230 causes flanges 230 to separate from each other, expanding the working channel of cannula 228.

Figure 13:
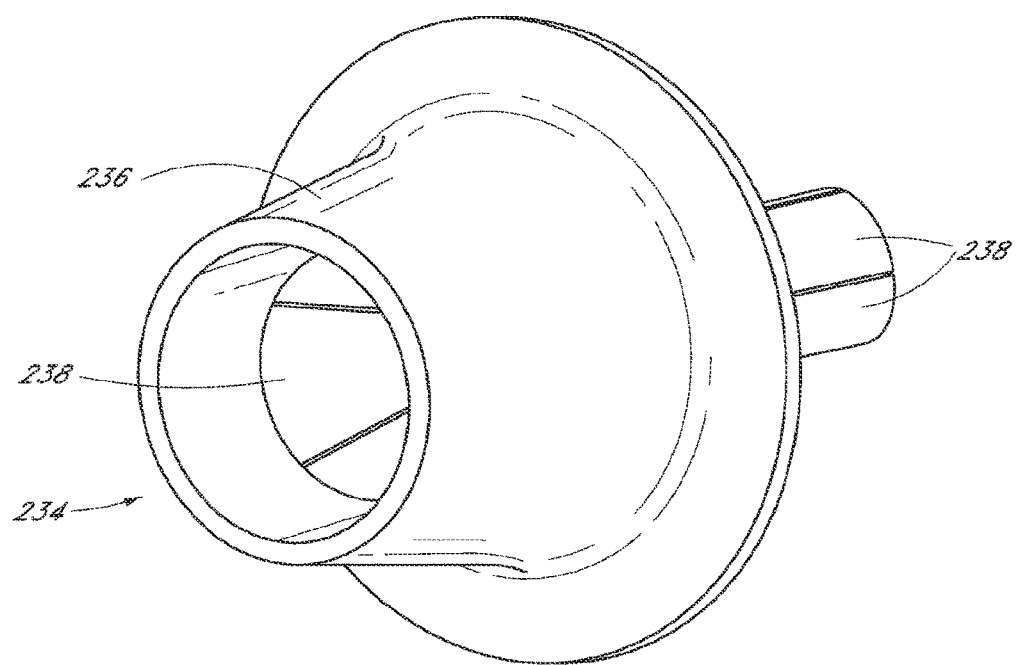
FIG. 13 is a perspective of yet another example of a cannula in accordance with the present invention.

FIG. 13 is yet another example of a cannula 234 having a housing 236 with several flanges 238 attached. In this embodiment, housing 236 is a single molded device having a tapering entry lumen 240 with flanges 238 attached by any acceptable method such as adhesive. The entry lumen defines the maximum working channel allowed by cannula 234 and flanges are attached such that they are able to expand and deflect beginning immediately at the interface with housing 236 at lumen 240. In this embodiment, the cannula 234 may be formed by insert molding a tube (e.g., nitinol) composed of flanges 238 (e.g. super elastic nitinol) into polymer housing 236. Cannula 234 has several specific features, including several slits (five in this example) distributed substantially symmetrically about the cannula body, a wider proximal end than distal end, and the wider proximal end of flanges 238 is within housing 236 that is placed on the tissue outside the surgical site.

Figure 14:
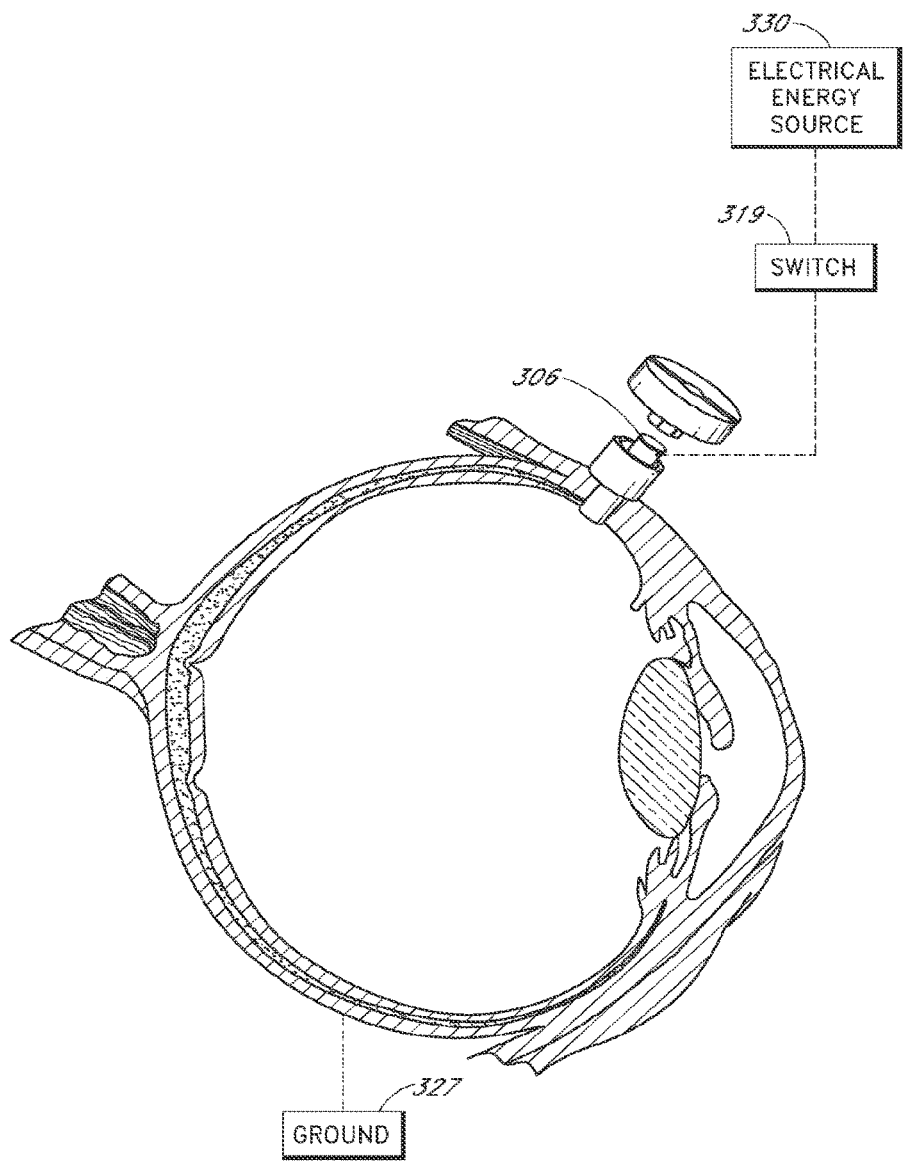
FIG. 14 is a perspective of yet another example of a cannula in accordance with the present invention.

In certain embodiments, as shown in FIG. 14, an expandable member 306 similar to the expandable member 106, is coupled to an electrical energy source 330. The electrical energy source 330 can be configured to apply a current to the expandable member 306, which can be controlled by a switch 319. Depending on the polarity of the current, the expandable member 306 can be configured to increase or decrease in diameter. In certain embodiments, the amount of electrical current applied to the expandable member ranges between 1 nanoamp and 100 microamps. In certain embodiments, the electrical current does not damage or injure the eye or the surrounding tissue, as the current may be insulated from the tissue (e.g., by an insulating layer). Depending on the current passed through expandable member 306, for safety purposes, a grounding path, as is known, may be used to protect the patient and surrounding tissue from harm. A ground 327 is operatively connected to the eye 101 to assist in the grounding process.

In some embodiments, a proximal end of the expandable member 306 is coupled to the electrical energy source 330. The expandable member 306 can be part of a cannula system that can be anchored in the pars plana of an eyeball. The expandable member 306 can increase or decrease from one gauge to another when electrical energy is applied by the electrical energy source 330. The expandable member 306 can be extracted by reducing a diameter of the expandable member to a larger gauge by varying the electrical energy applied by the electrical energy source 330.

Figure 15A:
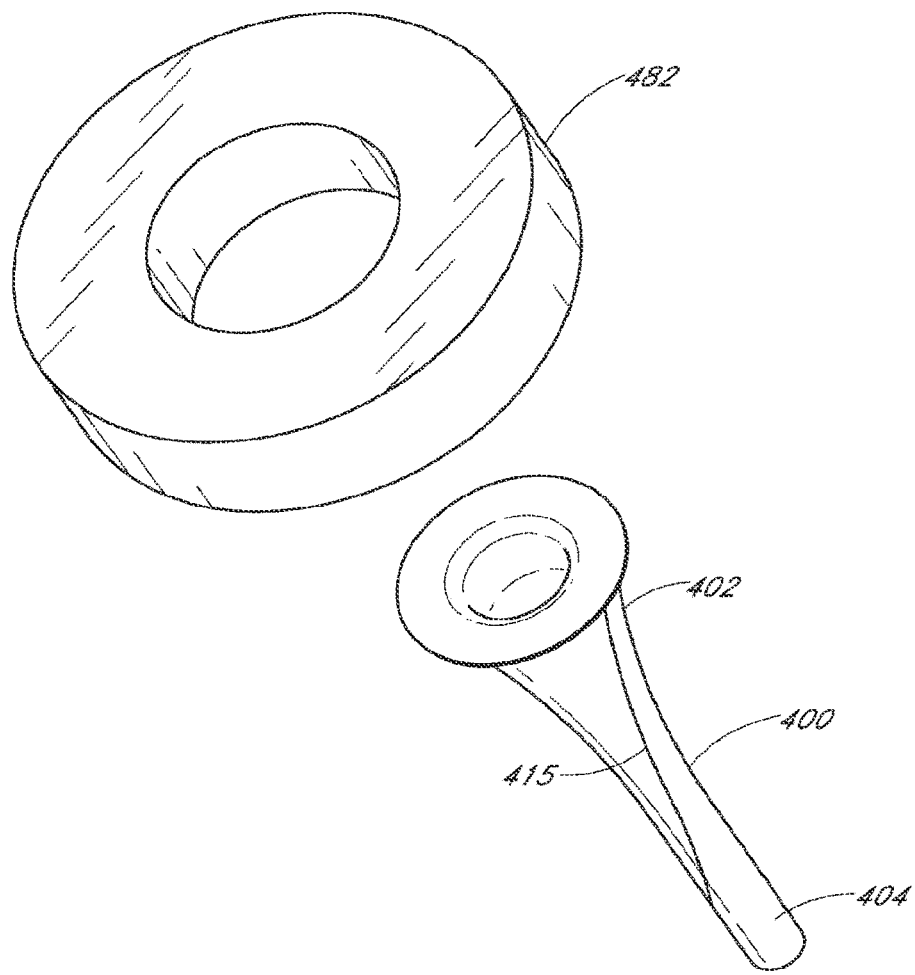
FIG. 15A is a perspective of yet another example of a cannula with upper housing in accordance with the present invention.

FIG. 15A is a perspective of yet another example of a cannula with upper housing in accordance with the present invention. The cannula includes an expandable member 400 including a proximal portion 402 and a distal portion 404. In an unexpanded state, the proximal portion 402 has a larger cross-sectional area than the distal portion 404 to form a generally conical shape or cone-like configuration. In some embodiments, the expandable member 400 comprises a foldable or winding coil that has an ending edge 415, as shown in FIG. 15A. In an embodiment, the ending edge 415 is positioned on the surface of the expandable member 400 diagonally relative to a longitudinal axis extending between the distal end and proximal end of the expandable member 400 because the diameter of the proximal end is larger than the diameter of the distal end of the expandable member 400. The ending edge 415 can comprise a substantially smooth edge, a curved edge, a slanted edge, a coating, or other edge configuration to prevent tissue from being captured by the ending edge 415 as the expandable member 400 expands and contracts. Also shown is an upper housing 482 which can couple with the expandable member 400. The expandable member 400 and upper housing 482 form an adjustable cannula system that can expand and contract via a mechanical force (e.g., a probe) as discussed with respect to FIG. 15C.

Figure 15B:
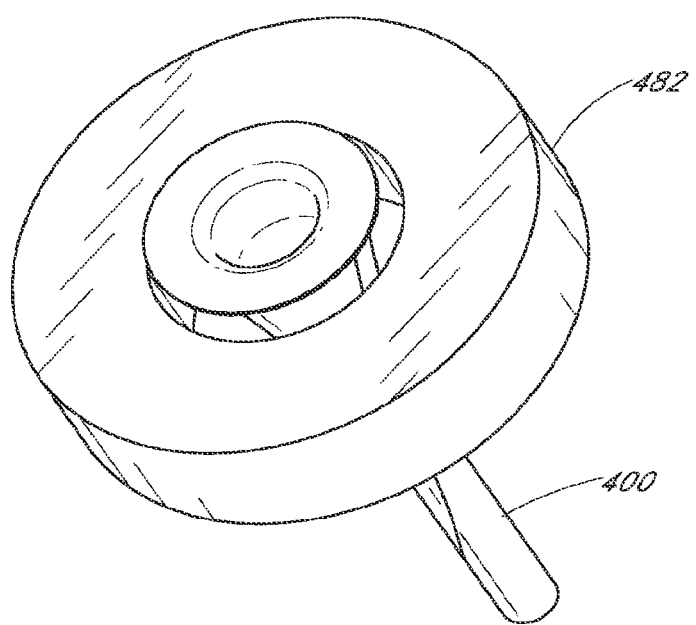
FIG. 15B illustrates the cannula of FIG. 15A being coupled to an upper housing.
Figure 15C:
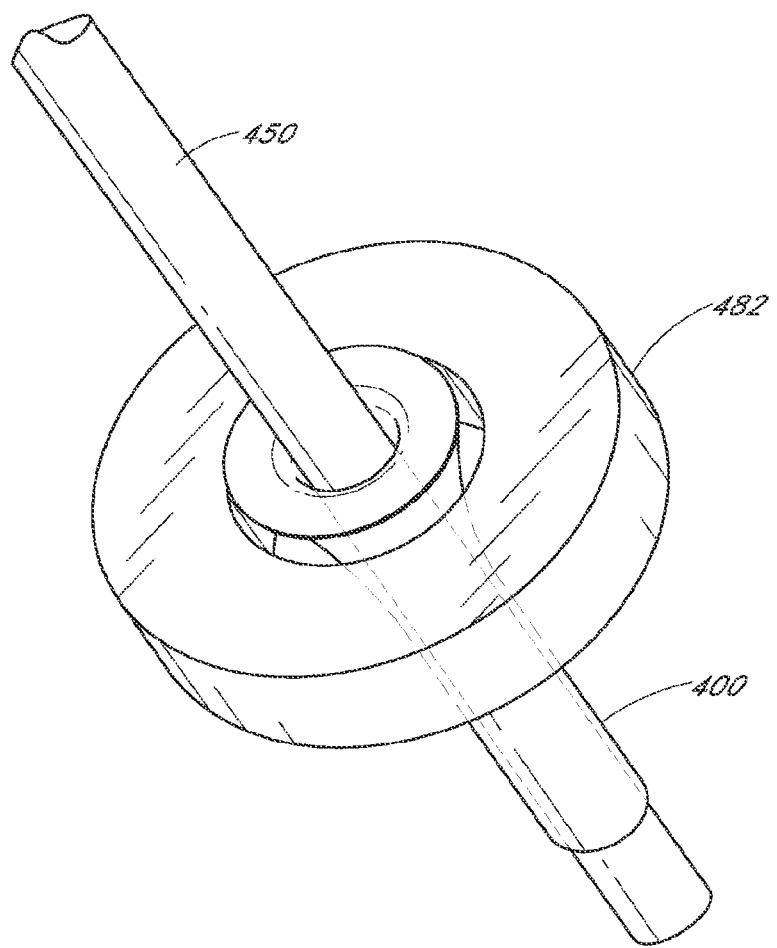
FIG. 15C illustrates the cannula of FIG. 15B being expanded via use of a probe.

FIG. 15B illustrates the cannula of FIG. 15A being coupled or being inserted into an upper housing. The expandable member 400 of the cannula can be coupled to the upper housing 482 by any of the methods described above or can merely placed into the housing be snapped into place or be held in place due to frictional forces. For example, the expandable member 400 can include a tab capable of mating with a mateable portion (e.g., a slot) in the upper housing 482. In other embodiments, the expandable member 400 of the cannula and the upper housing 482 are formed as a single piece.

FIG. 15C illustrates the cannula of FIG. 15B being expanded via use of a probe. Like the cannula with slits described in above embodiments, the cannula having expandable member 400 in the form of a winding coil can also be expanded using a probe 450. As the probe is inserted into the cannula, the coiled portion at the distal end and at the intermediate portion begin to unwind to expand the internal working channel of the expandable member 400. In an embodiment, the proximal end does not expand because the proximal end of the expandable member 400 comprises a larger diameter than the diameter of the intermediate and distal portion. In some embodiments, the probe 450 is hollow, such that instruments, tools or tissue can be introduced through the probe. In some embodiments, the probe is an instrument or device that can include, for example, biopsy devices, scissors, tissue cutting and/or removal devices, draining devices, light sources, fluid infusion devices, and the other surgical instruments. While introducing the probe 450 into the expandable member 400 can result in expansion, removing the probe 450 from the expandable member 400 can result in contraction. Advantageously, like the other cannulas described above, the cannula described in FIGS. 15A-15C allows for introduction into tissue a cannula of narrow size that can controllably expand only if desired to larger sizes, thereby reducing the risk of injury of tissue and the need for sutures. Further, the cannula illustrated in FIGS. 15A-15C does not require twisting of the housing portion to expand or contract the diameter of the cannula, rather expansion and contraction occurs when a probe is inserted or removed from the cannula.

In some embodiments, the cannula 400 is of a material that is sufficiently elastic to allow for expansion of one or more coils, and sufficiently stiff to prevent collapse of the cannula during the expansion. Such material can include various plastics and metals (including metal alloys), as well as plastics with metal embedded therein. The geometry of the cannula 400 can also be controlled to minimize the damage to the surrounding tissue performed by the cannula 400 when it is introduced and/or expanded within an eye. Controlling the geometry can provide for sufficient stiffness, while providing sufficient flexibility to the cannula to allow for expansion.

Figure 16A:
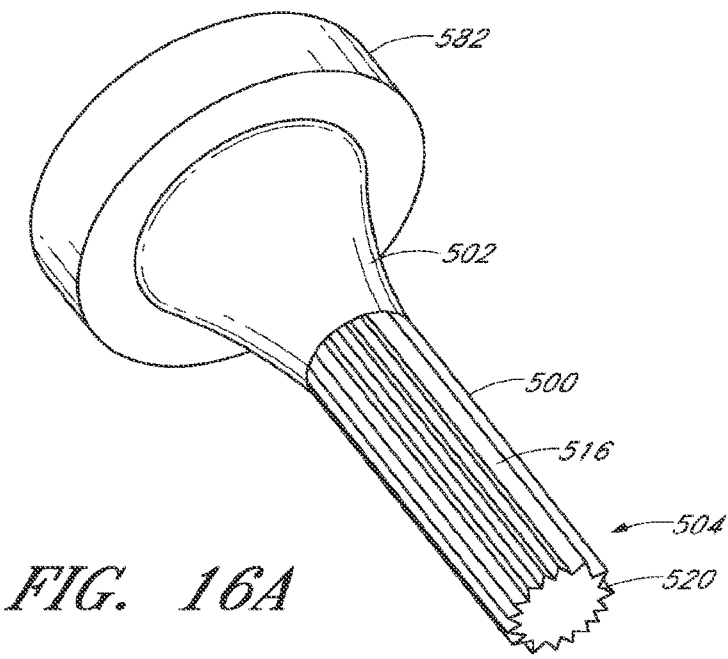
FIG. 16A is a perspective of yet another example of a cannula with housing in accordance with the present invention.

FIG. 16A is a perspective of yet another example of a cannula with housing in accordance with the present invention. The cannula includes an expandable member 500 including a proximal portion 502 and a distal portion 504, wherein the proximal portion 502 has a larger cross-sectional area than the distal portion 504 in an unexpanded state. Along the body of the expandable member 500 are a plurality of flutes or folds 516. In the illustrated embodiment, the folds 516 extend along a majority of the length of the expandable member 500, from the proximal portion 502 to a furthest most distal end 520 of the distal portion 504, although the folds need not assume such a length in every embodiment (for example, the proximal portion need not be fluted). Due to the folds 516, the distal end 520 includes a number of edge points as shown in FIG. 16A. Also shown is a housing 582 which is coupled with the expandable member 500. The expandable member 500 and housing 582 form an adjustable cannula system that can expand and contract via a mechanical force (e.g., a probe) as discussed with respect to FIG. 15C. In some embodiments, the cannula can be formed at least in part of a metal, metal alloy (e.g., nitinol) or polymer, or any combination thereof.

Figure 16B:
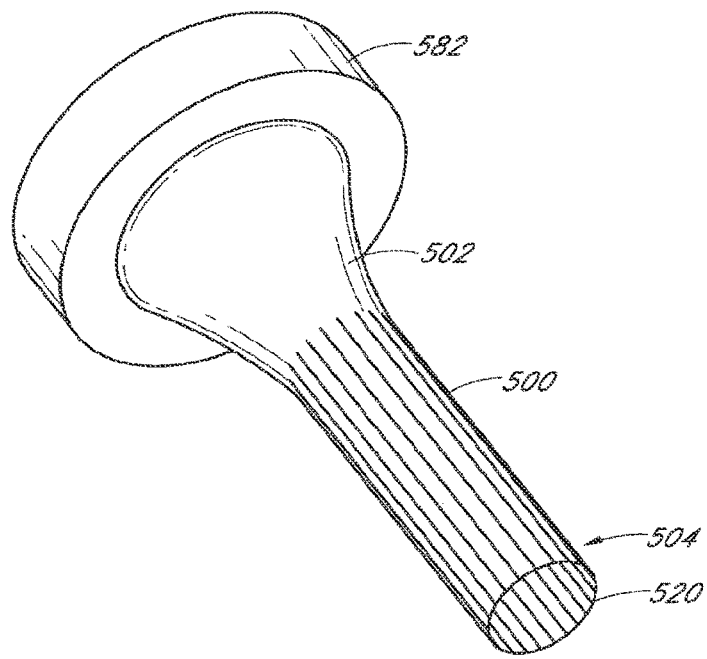
FIG. 16B illustrates the cannula of FIG. 16A in an expanded form.

FIG. 16B illustrates the cannula of FIG. 16A in an expanded form that has been expanded via use of a probe. As the probe is inserted through the expandable member 500, the folds 516 of the expandable member 500 accommodate expansion. As shown in FIG. 16B, upon expansion, the folds of the expandable member 500 can expand outward, such that the expandable member 500 is left with a substantially smooth surface. Also, upon expansion, the expandable member 500 can assume a cylindrical shape such that the distal end 520 appears circular. Advantageously, like the other cannulas described above, the cannula described in FIGS. 16A and 16B allows for introduction into tissue a cannula of narrow size that can controllably expand only if desired to larger sizes, thereby reducing the risk of injury of tissue and the need for sutures.

Figure 17A:
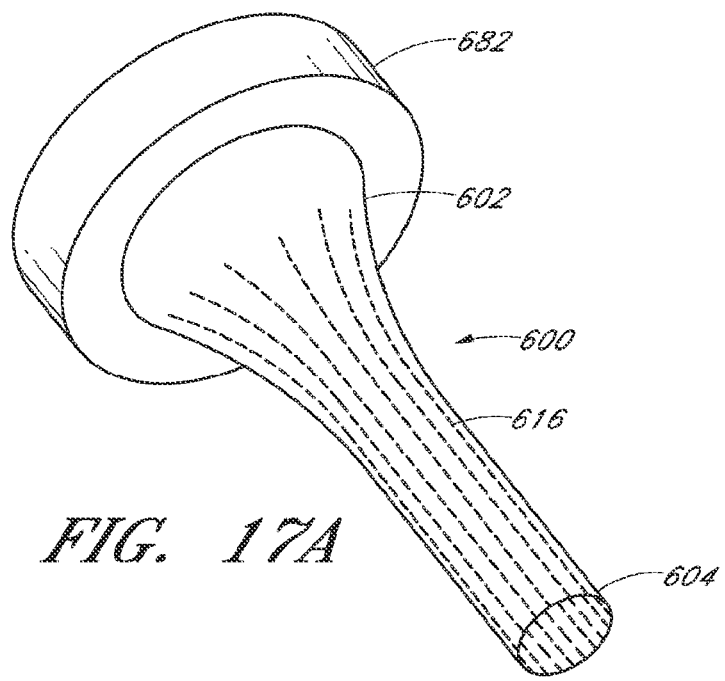
FIG. 17A is a perspective of yet another example of a cannula with housing in accordance with the present invention.
Figure 17B:
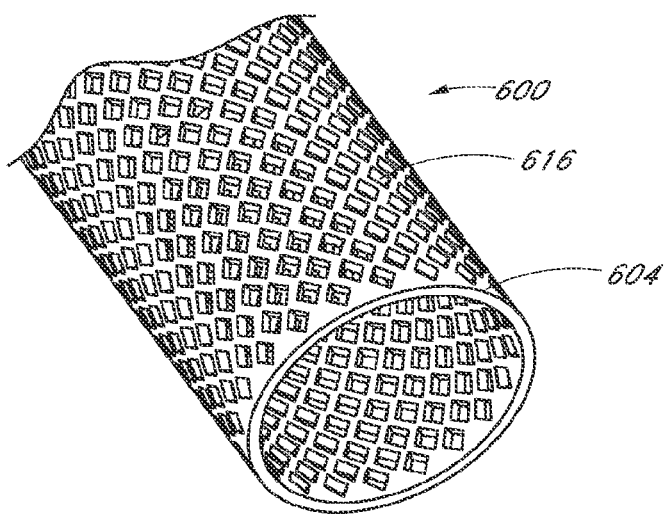
FIG. 17B illustrates a distal portion of the cannula of FIG. 17A in an expanded form.

FIG. 17A is a perspective of yet another example of a cannula with housing in accordance with the present invention. The cannula includes an expandable member 600 including a proximal portion 602 and a distal portion 604, wherein the proximal portion 602 has a larger cross-sectional area than the distal portion 604 in an unexpanded state. Along the body of the expandable member 600 are a plurality of actuating elements 616 that can expand into a cross-hatched or cage pattern (as shown in FIG. 17B). In the illustrated embodiment, the actuating elements 616 extend along a majority of the length of the expandable member 600, from the proximal portion 602 to the distal portion 604, although in other embodiments, the actuating elements 616 can extend a lesser portion along the length of the expandable member 600 (e.g., the proximal portion need not have the actuating elements). Also shown is a housing 682 which is coupled with the expandable member 600. The expandable member 600 and housing 682 form an adjustable cannula system that can expand and contract via a mechanical force (e.g., a probe) as discussed with respect to FIG. 15C. In some embodiments, the cannula can be formed at least in part of a metal, metal alloy (e.g., nitinol) or polymer, or any combination thereof.

FIG. 17B illustrates a distal portion of the cannula of FIG. 17A in an expanded form via use of a probe. As the probe is inserted through the expandable member 600, the actuating elements 616 of the expandable member 600 accommodate expansion. As shown in FIG. 17B, upon expansion, the actuating elements 616 can expand outward and form a cross-hatched or cage pattern. In some embodiments, the cannula in an expanded form can resemble a wire-frame. In some embodiments, the exposed cross-hatched areas can interact with tissue to provide a seal for the cannula, while in other embodiments, the exposed cross-hatched areas can be surrounded by a thin film or membrane that can be contractible with the cannula to prevent liquids and other materials form inadvertently entering and/or escaping the lumen of the cannula. Advantageously, like the other cannulas described above, the cannula described in FIGS. 17A and 17B allows for introduction into tissue a cannula of narrow size that can controllably expand only if desired to larger sizes, thereby reducing the risk of injury of tissue and the need for sutures.

Thus, there has been described several examples of adjustable cannulas that allow a small initial incision to be made but yet allow use of larger port sizes during surgery while allowing the incision to return to a size that may be self-sealing and without the need for sutures. The following are some comments regarding some possible variations of the examples described above. These statements and variations are not to be considered exhaustive or the only variations possible in accordance with the present invention, but only for further illustrative purposes.

In some embodiments, the adjustable cannula 200 can be tapered such that it is of a reduced diameter in a distal portion relative to a proximal portion. In some embodiments, the cannula 200 is configured to be naturally tapered upon entering a body cavity, while in other embodiments, the cannula 200 is configured to be naturally non-tapered but will taper in whole or in part upon expansion of the cannula. In some embodiments, the walls of the cannula 200 are tapered. The advantage of having a tapered cannula or tapered walls is that surrounding tissue is less likely to be disturbed around the narrowest sections of the tapered cannula 200, and certain tissue will only be affected if the cannula 200 is expanded.

In some embodiments, the cannula 200 comprises an adjustable seal located at a distal portion or proximal portion of the cannula, as is known, to prevent the escape of liquids and gases within the cannula, as well as the influx of unwanted materials into the cannula 200. As is known, the seal can comprise a film or diaphragm that adjusts with the cannula during expansion and contraction. In some embodiments, the seal can comprise a shutter ring or valve that adjusts into various positions (e.g., fully opened, partially opened, fully closed) in accordance with the state of the cannula. In some embodiments, like the slit openings, the adjustable seal can also interact with surrounding tissue such that when there is an opening in the seal, the surrounding tissue can help provide a blocking function.

Conditional language, such as, among others, "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Although this invention has been disclosed in the context of certain preferred embodiments and examples, it will be understood by those skilled in the art that the present invention extends beyond the specifically disclosed embodiments to other alternative embodiments or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

What is claimed is:

1. An adjustable cannula system for performing eye surgery, the system comprising:
   a bottom housing for placement on an eye, the bottom housing comprising first and second lumens and a first slot;
   an expandable member configured to increase and decrease from one diameter to another, the expandable member to be received in the first and second lumens of the bottom housing, the expandable member having a distal end for insertion into the eye, the expandable member including at least two protrusions protruding from only a proximal end of the expandable member, wherein the first slot engages one of the protrusions; and
   a top housing comprising a second slot configured to engage the other of the two protrusions, the top housing configured to control the diameter of the expandable member by rotating the top housing relative to the bottom housing.

2. The cannula system of claim 1, wherein a locking mechanism is configured to maintain the adjustable cannula at a selected diameter size.

3. The cannula system of claim 1, wherein the top and bottom housings together form a detent mechanism providing and maintaining a plurality of expandable member diameters when the top housing is rotated relative to the bottom housing.

4. The cannula system of claim 1, wherein the expandable tube comprises memory metal.

* * * * *